US007820695B2

(12) United States Patent
Weiner et al.

(10) Patent No.: US 7,820,695 B2
(45) Date of Patent: *Oct. 26, 2010

(54) SELECTIVE SEROTONIN RECEPTOR INVERSE AGONISTS AS THERAPEUTICS FOR DISEASE

(75) Inventors: David M. Weiner, San Diego, CA (US); Robert E. Davis, San Diego, CA (US); Mark R. Brann, Del Mar, CA (US)

(73) Assignee: ACADIA Pharmaceuticals, Inc., San Diego, CA (US)

( * ) Notice: Subject to any disclaimer, the term of this patent is extended or adjusted under 35 U.S.C. 154(b) by 1474 days.

This patent is subject to a terminal disclaimer.

(21) Appl. No.: 10/850,819

(22) Filed: May 21, 2004

(65) Prior Publication Data

US 2005/0261340 A1    Nov. 24, 2005

(51) Int. Cl.
    *A61K 31/445*    (2006.01)
    *A61K 31/137*    (2006.01)
    *A61P 25/24*     (2006.01)
(52) U.S. Cl. ........................... 514/317; 514/277
(58) Field of Classification Search ............. 514/224.5, 514/279, 595, 277, 317, 649
    See application file for complete search history.

(56) References Cited

U.S. PATENT DOCUMENTS

| | | | |
|---|---|---|---|
| 3,983,234 A | 9/1976 | Sayers | |
| 4,138,492 A | 2/1979 | Noverola et al. | |
| 4,255,432 A | 3/1981 | Kluge et al. | |
| 4,332,804 A | 6/1982 | Clark | |
| 4,353,900 A | 10/1982 | Clark | |
| 4,353,901 A | 10/1982 | Clark | |
| 4,367,232 A | 1/1983 | Boix-Igleasias et al. | |
| 4,853,394 A | 8/1989 | King et al. | |
| 5,025,013 A | 6/1991 | Barreau et al. | |
| 5,214,055 A | 5/1993 | Peglion et al. | |
| 5,216,165 A | 6/1993 | Mobilio et al. | |
| 5,461,066 A | 10/1995 | Gericke et al. | |
| 5,595,872 A | 1/1997 | Wetterau, II et al. | |
| 5,621,010 A | 4/1997 | Sueda et al. | |
| 5,707,798 A | 1/1998 | Brann | |
| 5,795,894 A | 8/1998 | Shue et al. | |
| 5,869,488 A | 2/1999 | Shue et al. | |
| 5,877,173 A | 3/1999 | Olney et al. | |
| 5,912,132 A | 6/1999 | Brann | |
| 5,955,281 A | 9/1999 | Brann | |
| 6,107,324 A | 8/2000 | Behan et al. | |
| 6,140,509 A | 10/2000 | Behan et al. | |
| 6,150,393 A | 11/2000 | Behan et al. | |
| 6,358,698 B1 | 3/2002 | Weiner et al. | |
| 6,479,480 B1 | 11/2002 | Moyes et al. | |
| 6,756,393 B2 | 6/2004 | Andersson et al. | |
| 6,815,458 B2 | 11/2004 | Andersson et al. | |
| 6,911,452 B2 | 6/2005 | Schlienger | |
| 7,022,698 B2 | 4/2006 | Hamied et al. | |
| 7,041,667 B1 | 5/2006 | Armour et al. | |
| 7,115,634 B2 | 10/2006 | Thurieau et al. | |
| 7,253,186 B2 | 8/2007 | Andersson et al. | |
| 2002/0004513 A1 | 1/2002 | Andersson et al. | |
| 2002/0156068 A1 | 10/2002 | Behan et al. | |
| 2002/0165225 A1 | 11/2002 | Hamied et al. | |
| 2004/0006081 A1 | 1/2004 | Burrows et al. | |
| 2004/0106600 A1 | 6/2004 | Andersson et al. | |
| 2004/0213816 A1 | 10/2004 | Weiner et al. | |
| 2005/0014757 A1 | 1/2005 | Andersson et al. | |
| 2005/0148018 A1 | 7/2005 | Weiner et al. | |
| 2005/0244862 A1 | 11/2005 | Brann | |
| 2005/0256108 A1 | 11/2005 | Schlienger | |
| 2006/0094758 A1 | 5/2006 | Andersson et al. | |
| 2006/0106063 A1 | 5/2006 | Thygesen et al. | |
| 2006/0111399 A1 | 5/2006 | Thygesen et al. | |
| 2006/0194778 A1 | 8/2006 | Andersson et al. | |
| 2006/0194834 A1 | 8/2006 | Andersson et al. | |
| 2006/0199794 A1 | 9/2006 | Schlienger | |
| 2006/0199818 A1 | 9/2006 | Andersson et al. | |
| 2006/0199842 A1 | 9/2006 | Weiner et al. | |
| 2006/0205710 A1 | 9/2006 | Schlienger et al. | |
| 2006/0205722 A1 | 9/2006 | Andersson et al. | |
| 2006/0205780 A1 | 9/2006 | Thygesen et al. | |
| 2006/0205781 A1 | 9/2006 | Thygesen et al. | |
| 2006/0264465 A1 | 11/2006 | Weiner et al. | |

(Continued)

FOREIGN PATENT DOCUMENTS

CA            984843        3/1976

(Continued)

OTHER PUBLICATIONS

Benfield P, Heel RC, Lewis SP, "Fluoxetine. A review of its pharmacodynamic and pharmacokinetic properties, and therapeutic efficacy in depressive illness," Drugs, 1986, 32(6), pp. 481-508.*
R&D Focus Drug News (Nov. 12, 2001).*
Goodman and Gilman, The Pharmacological Basis of Therapeutics, McGraw Hill, 1996, 9th ed., p. 434-435.*
Adam, et al. 1989. Effects of repeated ritanserin on middle-aged poor sleepers. *Psychopharmacology*, 99:219-221.
Adell, et al. 2005. Strategies for producing faster acting antidepressants. *Drug Discovery Today*, 10(8):578-585.
Akin, et al. 2004. Decreased serotonin 5-$HT_{2A}$ receptor-stimulated phosphoinositide signaling in fibroblasts from melancholic depressed patients. *Neuropsychopharmacology*, 29:2081-2087.
Alvisi, N. 1892. Sulla formazione di derivati pirazolici dalle dicloridrine e dalla tribromidrina della glicerina ordinaria, *Gazz. Chem. Ital.* 22:158-168.

(Continued)

*Primary Examiner*—Sreeni Padmanabhan
*Assistant Examiner*—Sahar Javanmard
(74) *Attorney, Agent, or Firm*—Jones Day

(57) ABSTRACT

Disclosed herein are pharmaceutical compositions comprising an inverse serotonin receptor agonist or a serotonin receptor antagonist and an anti-psychotic agent. Disclosed herein are also methods of treating psychotic disorders using the disclosed pharmaceutical compositions.

13 Claims, No Drawings

U.S. PATENT DOCUMENTS

| | | | |
|---|---|---|---|
| 2006/0264466 | A1 | 11/2006 | Weiner et al. |
| 2006/0286610 | A1 | 12/2006 | Brann |
| 2006/0292606 | A1 | 12/2006 | Brann |

FOREIGN PATENT DOCUMENTS

| | | | |
|---|---|---|---|
| EP | 0 005 318 A1 | | 11/1979 |
| EP | 0 061 333 A1 | | 9/1982 |
| EP | 0 379 441 A1 | | 7/1990 |
| EP | 0 548 015 A1 | | 6/1993 |
| EP | 0 260 070 B1 | | 8/1993 |
| EP | 0 625 507 A2 | | 11/1994 |
| EP | 1 656 938 A1 | | 5/2006 |
| FR | 2802206 A1 | | 6/2001 |
| HU | 157325 | | 3/1998 |
| JP | 51052176 | | 5/1976 |
| JP | 5208517 A | | 7/1977 |
| WO | WO 94/27967 A1 | | 12/1994 |
| WO | WO 97/08166 A1 | | 3/1997 |
| WO | WO 97/11940 A1 | | 4/1997 |
| WO | WO 97/38665 A2 | | 10/1997 |
| WO | WO 97/38984 A1 | | 10/1997 |
| WO | WO 98/11128 A1 | | 3/1998 |
| WO | WO 98/17646 A1 | | 4/1998 |
| WO | WO 98/44921 A1 | | 10/1998 |
| WO | WO 98/50534 A1 | | 11/1998 |
| WO | WO 99/52927 A1 | | 10/1999 |
| WO | WO 00/23076 A1 | | 4/2000 |
| WO | WO 00/56335 A1 | | 9/2000 |
| WO | WO 00/59497 A1 | | 10/2000 |
| WO | WO 00/69810 A1 | | 11/2000 |
| WO | WO 01/44191 A1 | | 6/2001 |
| WO | WO 01/66521 | * | 9/2001 |
| WO | WO 01/66521 A1 | | 9/2001 |
| WO | WO 01/87839 A1 | | 11/2001 |
| WO | WO 02/24649 | | 3/2002 |
| WO | WO 02/076464 A1 | | 10/2002 |
| WO | WO 02/079186 A2 | | 10/2002 |
| WO | WO 03/057698 A2 | | 7/2003 |
| WO | WO 03/057698 A3 | | 7/2003 |
| WO | WO 03/062206 A2 | | 7/2003 |
| WO | WO 03/062206 A3 | | 7/2003 |
| WO | WO 03/070246 A1 | | 8/2003 |
| WO | WO 03/086400 A1 | | 10/2003 |
| WO | WO 04/000808 A2 | | 12/2003 |
| WO | WO 04/000808 A3 | | 12/2003 |
| WO | WO 2004/009549 A2 | | 1/2004 |
| WO | WO 2004/039322 A2 | | 5/2004 |
| WO | WO 2004/064738 A2 | | 8/2004 |
| WO | WO 2004/064738 A3 | | 8/2004 |
| WO | WO 2004/064753 A2 | | 8/2004 |
| WO | WO 2004/072034 A1 | | 8/2004 |
| WO | WO 2005/053796 A1 | | 6/2005 |
| WO | WO 2005/063254 A2 | | 7/2005 |
| WO | WO 2005/112927 A | | 12/2005 |
| WO | WO 2006/036874 A1 | | 4/2006 |
| WO | WO 2006/037043 A1 | | 4/2006 |
| WO | WO 2006/104826 | | 10/2006 |

OTHER PUBLICATIONS

Antilla, et al. 2001. Copper-catalyzed coupling of arylboronic acids and amines. *Organic Letters*, 3(13):2077-2079.

Antilla, et al. 2002. The copper-catalyzed N-arylation of indoles. *J. Am. Chem. Soc.*, 124:11684-11688.

Archibald, et al., 1974 "Benzamidopiperdines. 2. Heterocyclic Compounds Related to Indoramin" *J. Medicinal Chemistry*, 17(7):736-739.

Archibald, et al., 1974 "Benzamidopiperdines. 3. Heterocyclic Compounds Related to Indoramin" J. Medicinal Chemistry, 17(7):-739-744.

Archibald, et al., 1974 "1,4-Bis-(2-indol-3-ylethyl)piperdines" J. Medicinal Chemistry, 17(7):-745-747.

Artico, et al. 1992. Aromatic hydrazides as specific inhibitors of bovine serum amine oxidase. *Eur. J. Med. Chem.*, 27:219-228.

Bakshi, et al. 1994. Clozapine antagonizes phencyclidine-induced deficits in sensorimotor gating of the startle response. *The Journal of Pharmacology and Experimental Therapeutics*, 271(2):787-794.

Barchas, J. 1973. *Serotonin and Behavior.* New York: Academic Press.

Barnes, et al. 1999. A review of central 5-HT receptors and their function. *Neuropharmacology*, 38:1083-1152.

Barr, et al. 1997. Agonist-independent activation of $G_z$ by the 5-hydroxytryptamine$_{1A}$ receptor co-expressed in *Spodoptera frugiperda* cells. *The Journal of Biological Chemistry*, 272(52):32979-32987.

Bassus, et al. 1974. Psychotropies potentiels. X. Synthèse de butyrophénones à cycle pipéridine-spiro-tétrahydrooxazinone douées d'activité neuroleptique. *Eur. J. Med. Chem.—Chimica Therapeutica*, 9(4):416-423.

Bennett, et al. 1993. Suppression of dyskinesias in advanced Parkinson's disease. II. Increasing daily clozapine doses suppress dyskinesias and improve parkinsonism symptoms. *Neurology*, 43:1551-1555.

Bhatia, et al. 1996. 5-Lipoxygenase inhibitors: Synthesis and structure-activity relationships of a series of 1-Aryl-2$H$,4$H$-tetrahydro-1,2,4-triazin-3-ones. *J. Med. Chem.*, 39:3938-3950.

Biagi, et al. 1988. 1,2,3-Triazoles: Structural changes on two effective inhibitors of the prostaglandin synthesis in vitro. *Farmaco Ed. Sci.*, 43:597-612.

Bibbiani, et al. 2001. Serotonin 5-HT1A agonist improves motor complications in rodent and primate parkinsonian models. *Neurology*, 57:1829-1834.

Birkmayer, et al. 1974. Nucleus ruber and L-Dopa psychosis: Biochemical post-mortem findings. *Journal of Neural Transmission*, 35:93-116.

Blakley, et al. 2001. Bidirectional changes in ethanol consumption in rats with site-specific antisense down-regulation of 5-hydroxytryptamine$_{2A}$ receptors in brain. *The Journal of Pharmacology and Experimental Therapeutics*, 299(1):277-289.

Blier, et al. 2001. Putative mechanisms of action of antidepressant drugs in affective and anxiety disorders and pain. *Journal of Psychiatry & Neuroscience*, 26(1):37-43.

Blier, et al. 2005. Potential mechanisms of action of atypical antipsychotic medications in treatment-resistant depression and anxiety. *J. Clin. Psychiatry*, 66(suppl 8):30-40.

Bond et al. 1995. Physiological effects of inverse agonists in transgenic mice with myocardial overexpression of the $\beta_2$-adrenoceptor. *Nature*, 374:272-276.

Boullin D. J. 1978. *Serotonin In Mental Abnormalities* (p. 316). New York: Wiley.

Brown, et al. 1924. Catalytic alkylation of aniline, *J. Am. Chem. Soc.*, 46(8):1836-1839.

Buchi et al. 1969. Synthesis of (±)-nuciferal. *J. Org. Chem.*, 34(4):1122-1123.

Butcher, et al. 1970. L-Dopa induced changes in central monoamine neurons after peripheral decarboxylase inhibition. *Letters to the Editor, J. Pharm. Pharmac.*, 22:313-316.

Buu-Hoi, et al. 1951. Further studies in the alkylation of phenols and thiophenols, *J. Org. Chem.*, 16:988-994.

Cacchi, et al. 2003. Palladium-catalyzed reaction of aryl iodides with acetic anhydride. A carbon monoxide-free synthesis of acetophenones. *Organic Letters*, 5(3):289-291.

Carman, et al. 1998. A further synthesis of an analogue of the antifungal/antiherbivore lipid from avocado. *Aust. J. Chem.*, 51:955-959.

Caroon, et al. 1981. Synthesis and antihypertensive activity of a series of 8-substituted 1-Oxa-3,8-diazaspiro[4.5]decan-2-ones. *J. Med. Chem.*, 24:1320-1328.

Carroll, et al. 1992. Synthesis and muscarinic receptor activity of ester derivatives of 2-substituted 2-azabicyclo[2.2.1]heptan-5-ol and -6-ol. *J. Med. Chem.*, 35:2184-2191.

Catarzi, et al. 2001. Synthesis, ionotropic glutamate receptor binding affinity, and structure-activity relationships of a new set of 4,5-dihydro-8-heteroaryl-4-oxo-1,2,4-triazolo[1,5-a]quinoxaline-2-carboxylates analogues of TQX-173. *J. Med Chem.*, 44:3157-3165.

Cerione, et al. 1984. The mammalian $\beta_2$-adrenergic receptor: Reconsitution of functional interactions between pure receptor and pure stimlatory nucelotide binding protein of the adenylate cyclase system. *Biochemistry*, 23:4519-4525.

Chemical Abstracts, 73:25305. Benke, et al. 1970.

Chemical Abstracts, 128:111548. Brann, M. R. 1998. Identification of ligands by selective amplification of cells transfected with receptors and marker enzymes.

Cherkasov, et al. 1985. Organothiophosphorus reagents in organic synthesis. *Tetrahedron*, 41(13):2567-2624.

Clark et al. 1983. Antihypertensive 9-substituted 1-Oxa-4,9-diazaspiro[5.5]undecan-3-ones. *J. Med. Chem.*, 26:855-861.

Clifton, et al. 1982. Arylethanolamines Derived from Salicyclamide with α- and β-Adrenoceptor Blocking Activities. Preparation of Labetalol, its Enantiomers, and Related Salicyclamides. *J. Med. Chem.*, 25:670-679.

DeClerck, et al. 1987. Increase in slow-wave sleep in humans with the serotonin-$S_2$ antagonist ritanserin. *Current Therapeutic Research*, 41(4):427-432.

Delecluse, et al. 1998. A case of tardive tremor successfully treated with clozapine. *Movement Disorders*, 13(5):846-847.

Dunn, et al. 1986. Analgetic and antiinflammatory 7-aroylbenzofuran-5-ylacetic acids and 7-aroylbenzothiophene-5-ylacetic acids. *J. Med. Chem.*, 29:2326-2329.

Durif, et al. 1997. Low-dose clozapine improves dyskinesias in Parkinson's disease. *Neurology*, 48:658-662.

Eichelbaum, et al. 1996. Influence of pharmacogenetics on drug disposition and response. *Clinical and Experimental Pharmacology and Physiology*, 23:983-985.

Emerson, et al. 1938. The reductive alkylation of aniline. *J. Am. Chem. Soc.*, 60:2023-2025.

Ermakov, et al. 1981. Use of Mass spectrometry in structural and stereochemical studies. *Chemistry of Heterocyclic Compounds*, 1:72-77.

Everett, et al. 1970. L-Dopa: Effect on concentrations of dopamine, norepinephrine, and serotonin in brains of mice. *Science*, 168:849-850.

Factor, et al. 1992. Clozapine prevents recurrence of psychosis in Parkinson's disease. *Movement Disorders*, 7(2):125-131.

Factor, et al. 2001. Clozapine for the treatment of drug-induced psychosis in Parkinson's disease: Results of the 12 week open label extension in the PSYCLOPS trial. *Movement Disorders*, 16(1):135-139.

Finar, et al. 1954. The preparation and properties of some derivatives of 1-phenylpyrazole, *J. Chem. Soc.*, pp. 2293-2298.

Fišera, et al. 1994. Synthesis of spiro-substituted 1,3-oxazines by a new sequence leading to spiroheterocycles. *Monatshefte für Chemie*, 125:909-919.

Friedman, J. H. 1994. Clozapine treatment of psychosis in patients with tardive dystonia: Report of three cases. *Movement Disorders*, 9(3):321-324.

Friedman, et al. 1999. Low-dose clozapine for the treatment of drug-induced psychosis in Parkinson's disease. *N. Engl. J. Med.*, 340(10):757-763.

Friedman, et al. 2000. Atypical antipsychotics in the treatment of drug-induced psychosis in Parkinson's disease. *Movement Disorders*, 15(2):201-211.

Fuller, R. W. 1982. Drugs acting on serotonergic neuronal systems. In N. N. Osborne (Ed.), *Biology of Serotonergic Transmission*, Chap. 9, pp. 221-247. New York: Wiley.

Gainetdinov, et al. 2001. Genetic animal models: Focus on schizophrenia. *Trends in Neurosciences*, 24(9)527-533.

Gamma, et al. 2000. 3,4-Methylenedioxymethamphetamine (MDMA) modulates cortical and limbic brain activity as measured by $[H_2^{15}O]$-PET in healthy humans. *Neuropsychopharmacology*, 23(4):388-395.

Gawley, R. E., & Aubé, J. 1996. *Principles of Asymmetric Synthesis*. New York: Pergamon.

Gershon, M. D., Mawe, G. M., & Branchek, T. A. 1989. 5-Hydroxytryptamine and enteric neurones. In J. R. Fozard (Ed.), *The Peripheral Actions of 5-Hydroxytryptamine* (pp. 247-273). New York: Oxford University Press.

Gillman, P. K. 2005. Monoamine oxidase inhibitors, opioid analgesics and serotonin toxicity. *British Journal of Anaesthesia*, 95(4):434-441.

Glennon, R. A. 1990. Serotonin receptors: Clinical implications. *Neuroscience & Biobehavioral Reviews*, 14:35-47.

Gooβen, et al. 2001. Palladium-catalyzed synthesis of aryl ketones from boronic acids and carboxylic acids or anhydrides. *Angew. Chem. Int. Ed.*, 40:3458-3460.

Gstach et al. 1990. Rearrangement of 3,3-disubstituted 1-aryl-4,5-dihydro-5-oxo-3H-1,2,4-triazolium tetrafluoroborates; Part 1. A versatile synthesis of 1,5-disubstituted 2-aryl-1,2-dihydro-3H-1,2,4-triazol-3-one tetrafluoroborates. *Synthesis*, pp. 803-808.

Guthrie, et al. 1993. The tetrahedral intermediate from the hydration of N-methylformanilide. *Can. J. Chem.*, 71:2109-2122.

Harper, et al. 1964. The chemistry and pharmacology of some 4-aminopiperidines and their derivatives. *J. Med. Chem.*, 44:729-732.

Hartwig, J. F. 1998. Transition metal catalyzed synthesis of arylamines and aryl ethers from aryl halides and triflates: Scope and mechanism. *Angew. Chem. Int. Ed.*, 37:2047-2067.

Herrick-Davis, et al. 2000. Inverse agonist activity of atypical antipsychotic drugs at human 5-hydroxytryptamine2C receptors. *The Journal of Pharmacology and Experimental Therapeutics*, 295(1):226-232.

Hickinbottom, W. J. 1930. The preparation of secondary alkylarylamines and their purification. *J. Chem. Soc.*, pp. 992-994.

Hirst, et al. 1895. A method for preparing the formyl derivatives of the aromatic amines. *J. Chem. Soc.*, 67:829-831.

Idzikowski, et al. 1991. A dose response study examining the effects of ritanserin on human slow wave sleep. *Br. J. Clin. Pharmac.*, 31:193-196.

Irikura et al., 1971 "New Anticulcer Agents. 1. Synthesis and Biological Activities of 1-Acyl-2-,-3-, -4- substituted Benzamidopiperdines" *J. Medicinal Chemistry* 14(4): 357-361.

Jaeger, et al. 1941. Two ketones of the stilboestrol group. *J. Chem. Soc.*, 744-747.

Julius, et al. 1990. The 5HT2 receptor defines a family of structurally distinct but functionally conserved serotonin receptors. *Proc. Natl. Acad. Sci. USA*, 87:928-932.

Kalgutkar, et al. 1995. Selective inhibitors of monoamine oxidase (MAO-A and MAO-B) as probes of its catalytic site and mechanism. *Medicinal Research Reviews*, 15(4)325-388. XP002034298.

Kanayama, et al. 2005. New treatment of lumbar disc herniation involving 5-hydroxytryptamine$_{2A}$ receptor inhibitor: A randomized controlled trial. *J. Neurosurg: Spine*, 2:441-446.

Klapars, et al. 2001. A general and efficient copper catalyst for the amidation of aryl halides and the N-arylation of nitrogen heterocycles. *J. Am. Chem. Soc.*, 123:7727-7729.

Klapars, et al. 2002. A general and efficient copper catalyst for the amidation of aryl halides. *J. Am. Chem. Soc.*, 124:7421-7428.

Kuehne, et al. 1991(a). Enantioselective syntheses of vinblastine, leurosidine, vincovaline, and 20'-*epi*-vincovaline. *J. Org. Chem.*, 56(2):513-528.

Kuehne, et al. 1991(b). Total syntheses of *Yohimbe* alkaloids, with stereoselection for the normal, allo, and 3-epiallo series, based on annelations of 4-methoxy-1,2-dihydropyridones. *J. Org. Chem.*, 56(8):2701-2712.

Kwong, et al. 2002(a). Copper-catalyzed coupling of alkylamines and aryl iodides: An efficient system even in an air atmosphere. *Organic Letters*, 4(4):581-584.

Kwong, et al. 2002(b). A general, efficient, and inexpensive catalyst system for the coupling of aryl iodides and thiols. *Organic Letters*, 4(20):3517-3520.

Kwong, et al. 2003. Mild and efficient copper-catalyzed amination of aryl bromides and primary alkylamines. *Organic Letters*, 5(6):793-796.

Landini, et al. 1974. A convenient synthesis of primary and secondary dialkyl and aryl alkyl sulfides in the presence of phase-transfer catalysts. *Synthesis*, pp. 565-566.

Landolt, et al. 1999. Serotonin-2 receptors and human sleep: Effect of a selective antagonist on EEG power spectra. *Neuropsychopharmacology*, 21(3):455-466.

Leysen, et al. 1978. Serotonergic component of neuroleptic receptors. *Nature*, 272:168-171.

Li, G. Y. 2002. Highly active, air-stable palladium catalysts for the C-C and C-S bond-forming reactions of vinyl and aryl cholrides: Use of commercially available $[(t\text{-Bu})_2P(OH)]_2PdCl_2$, $[(t\text{-Bu})_2P(OH)PdCl_2]_2$, and $[[(t\text{-Bu})_2PO \ldots H \ldots OP(t\text{-Bu})_2]PdCl]_2$ as catalysts. *J. Org. Chem.*, 67:3643-3650.

Liechti, et al. 2001. Effects of MDMA (ecstasy) on prepulse inhibition and habituation of startle in humans after pretreament with Citalopram, Haloperidol, or Ketanserin. *Neuropsychopharmacology*, 24(3):240-252.

Linder, et al. 1997. Pharmacogenetics: A laboratory tool for optimizing therapeutic efficiency. *Clinical Chemistry*, 43(2):254-266.

Lowe, et al. 1994. Aza-tricyclic substance P antagonists. *J. Med. Chem.*, 37:2831-2840.

Mansbach, et al. 1988. Dopaminergic stimulation disrupts sensorimotor gating in the rat. *Psychopharmacology*, 94:507-514.

Marek, et al. 2003. Synergistic action of $5\text{-HT}_{2A}$ antagonists and selective serotonin reuptake inhibitors in neuropsychiatric disorders. *Neuropsychopharmacology*, 28:402-412.

Marek, et al. 2005. The selective $5\text{-HT}_{2A}$ receptor antagonist M100907 enhances antidepressant-like behavioral effects of the SSRI fluoxetine. *Neuropsychopharmacology*, 30:2205-2215.

Mavunkel, et al. 1996. Synthesis and characterization of pseudopeptide bradykinin B2 receptor antagonists containing the 1,3,8-triazaspiro[4.5]decan-4-one ring system. *J. Med. Chem.*, 39:3169-3173.

Mayer, et al. 2003. Ritanserin improves sleep quality in narcolepsy. *Pharmacopsychiatry*, 364:150-155.

Meltzer, et al. 1995. Plasma clozapine levels and the treatment of L-DOPA-induced psychosis in Parkinson's disease. *Neuropsychopharmacology*, 12(1):39-45.

Meltzer, H. Y. 1999. The role of serotonin in antipsychotic drug action. *Neuropsychopharmacology*, 21(2S):106S-115S.

Meng, et al. 1991. Synthetic approaches toward glidobamine, the core structure of the glidobactin antibiotics. *Tetrahedron*, 47(32):62510-6264.

Micovic, et al. 1991. A simple method for preparation of secondary aromatic amines. *Synthesis*, 11:1043-1045.

Miyata, et al. 2000. Sarpogrelate, a selective $5\text{-HT}_{2A}$ serotonergic receptor antagonist, inhibits serotonin-induced coronary artery spasm in a porcine model. *Journal of Cardiovascular Pharmacology*, 35(2) 294-301.

Möehrle, et al. 1990. Sodium mercury edetate dehydrogenation of N-aliphatic substituted 1,2,3,6-tetrahydropyridine derivatives. *Arch. Pharm. (Weinheim)*, 323:109-115.

Moulignier, A. 1994. Récepteurs centraux de la sérotonine principaux aspects fondamentaux et fonctionnels application thérapeutiques. *Rev. Neurol.*, 150:3-15.

Moune, et al. 1997. Total synthesis of dolatrienoic acid: A subunit of dolastatin 14. *J. Org. Chem.*, 62:3332-3339.

Mullen et al. 2000. (-)-Spiro[1-azabicyclo[2.2.2]octane-3,5'-oxazolidin-2'one], a conformationally restricted analogue of acetylcholine, is a highly selective full agonist at the α7 nicotinic acetylcholine receptor. *J. Med. Chem.*, 43:4045-4050.

Muri, et al. 1998. Synthesis of new benzylic ethers of oximes derived from 1-phenyl-pyrazole compounds. *Synthetic Communications*, 28(7):1299-1321.

Ng, et al. 1970. L-dopa-induced release of cerebral monoamines. *Science*, 170:76-77.

Nigam, et al. 1957a. Studies with acetylenes. Part II. Some reactions of Grignard reagents with propargylic halides. Model linoleic and linolenic acid systems. *J. Chem Soc.*, pp. 3868-3873.

Nigam, et al. 1957b. The conversion of fatty acids into aldehydes. *J. Chem. Soc.*, pp. 3320-3321.

Nordstrom, et al. 1993. High $5\text{-HT}_2$ receptor occupancy in clozapine treated patients demonstrated by PET. *Psychopharmacology*, 110:365-367.

Ogawa, et al. 2005. Effects of R-102444 and its active metabolite R-96544, selective 5-HT2A receptor antagonists, on experimental acute and chronic pancreatitis: Additional evidence for possible involvement of 5-HT2A receptors in the development of experimental pancreatitis. European Journal of Pharmacology, 521:156-163.

Olah, et al. 1956. Notiz über die *n*-formylierung von aminen mit formylfluorid. *Chem. Ber.*, 89:2211-2212.

Old, et al. 2002. Efficient palladium-catalyzed *n*-arylation of indoles. *Organic Letters*, 2(10):1403-1406.

Pace, et al. 1991. A mutant α subunit of $G_{i2}$ induces neoplastic transformation of Rat-1 cells. *Proc. Natl. Acad. Sci. USA*, vol. 88:7031-7035.

Paiva, et al. 1988. Effects of ritanserin on sleep disturbances of dysthymic patients. *Psychopharmacology*, 96:395-399.

Patel, et al. 2004. The highly selective 5-hydroxytryptamine $(5\text{-HT})_{2A}$ receptor antagonist, EMD 281014, significantly increases swimming and decreases immobility in male congenital learned helpless rats in the forced swim test. *Synapse*, 52:73-75.

Pierce, et al. 1995. 5-hydroxytryptamine-induced synovial plasma extravasation is mediated via 5-hydroxytryptamine2A receptors on sympathetic efferent terminals. *The Journal of Pharmacology and Experimental Therapeutics*, 275(1):502-508.

Pollak, et al. 1999. Clozapine in drug-induced psychosis in Parkinson's disease. *The Lancet*, 353:2041-2042.

Read, W. T. 1922. Researches on hydantoins. Synthesis of the soporific, 4,4-phenylethyl-hydantoin(nirvanol). *J. Am. Chem. Soc.*, 44:1746-1755.

Ricci, A. 2000. *Modern Animation Methods*. New York: Wiley-VCH.

Rice, et al. 1955. Raney nickel catalyzed n-alkylation of aniline and benzidine with alcohols. *J. Am. Chem. Soc.*, 77:4052-4054.

Rubiralta, M., Giralt, E., & Diez, A. 1991. *Studies in Organic Chemistry 43. Piperidine: Structure, Preparation, Reactivity and Synthetic Applications of Piperidine and its Derivatives*. New York: Elsevier.

Ryckmans, T., et al., 2002. "First Dual $NK_1$ Antagonists-Serotonin Reuptake Inhibitors: Synthesis and SAR of a New Class of Potential Antidepressants," *Bioorganic & Medicinal Chemistry Letters*, 261-264.

Sadzot, et al. 1989. Hallucinogenic drug interactions at human brain $5\text{-HT}_2$ receptors: Implications for treating LSD-induced hallucinogenesis. *Psychopharmacology*, 98:495-499.

Saltzman, et al. 1991. Cloning of the human serotonin 5-HT2 and 5-HT1C receptor subtypes. *Biochemical and Biophysical Research Communications*, 181(3):1469-1478.

Saxena, et al. 1990. Cardiovascular effects of serotonin agonists and antagonists. *Journal of Cardiovascular Pharmacology*, 15(Supp. 7):S17-S34.

Scheibye, et al. 1978. Studies on organophosphorus compounds XXI. The dimer of *p*-methoxyphenylthionophosphine sulfide as thiation reagent. A new route to thiocarboxamides. *Bull. Soc. Chim. Belg.*, 87:229-238.

Schins, et al. 2003. Increased coronary events in depressed cardiovascular patients: $5\text{-HT}_{2A}$ receptor as missing link? *Psychosomatic Medicine*, 65:729-737.

Screttas, et al. 1978. Hydrolithiation of α-olefins by a regiospecific two-step process. Transformation of alkyl phenyl sulfides to alkyllithium reagents. *J. Org. Chem.*, 43(6):1064-1071.

Sharpley, et al. 1994. Slow wave sleep in humans: Role of $5\text{-HT}_{2A}$ and $5\text{-HT}_{2C}$ receptors. *Neuropharmacology*, 33(3/4):467-471.

Smith, et al. 1995. New spiropiperdines as potent and selective non-peptide tachykinin $NK_2$ receptor antagonists. *J. Med. Chem.*, 38(19):3772-3779.

Stefancich, et al. 1984. Agenti antiinfiammatori non-steroidei: Nota III—sintesi ed attività analgesica-antiinfiammatoria di 4-(pirrol-1-il)-fenilacetamidi e di 4-(pirrol-1-il)fenetilamina. *Farmaco Ed. Sci.*, 39(9):752-764.

Stryjer, et al. 2003. Treatment of neuroleptic-induced akathisia with the $5\text{-HT}_{2A}$ antagonist trazodone. *Clinical Neuropharmacology*, 26(3):137-141.

Tolstikov et al. 1991 "Synthesis and Reactivity of N-substituted aminoamides, antiarrhythmic and local anaesthetic activity" *Russian Chemical Reviews* 60(4):420434.

Tsukamoto, et al. 1995. Synthesis and structure-activity studies of a series of 1-oxa-2,8-diazaspiro[4.5]decan-3-ones and related compounds as $M_1$ muscarinic agonists. *Chem. Pharm. Bull.*, 43(9):1523-1529.

Vallar, et al. 1987. Altered $G_S$ and adenylate cyclase activity in human GH-secreting pituitary adenomas. *Nature*, 330:566-568.

Van Laar, et al. 2001. Subchronic effects of the GABA-agonist lorazepam and the 5-HT$_{2A/2C}$ antagonist ritanserin on driving performance, slow wave sleep and daytime sleepiness in healthy volunteers. *Psychopharmacology*, 154:189-197.

Varma, et al. 1999. Microwave-accelerated solvent-free synthesis of thioketones, thiolactones, thioamides, thionoesters, and thioflavonoids. *Organic Letters*, 1(5):697-700.

Viola, et al. 2002. Ritanserin, a serotonin-2 receptor antagonist, improves ultradian sleep rhythmicity in young poor sleepers. *Clinical Neurophysiology*, 113:429-434.

Vogel, A. I. 1948. Physical properties and chemical constitution. Part XIX. Five-membered and six-membered carbon rings. *J. Chem. Soc.*, pp. 1809-1813.

Vogl, et al. 2002. Palladium-catalyzed monoarylation of nitroalkanes. *J. Org. Chem.*, 67(1):106-111.

Wade, et al. 2000. Application of base cleavable safety catch linkers to solid phase library production. *J. Comb. Chem.*, 2(3):266-275.

Weiner, et al. 2001. 5-Hydroxytryptamine$_{2A}$ receptor inverse agonists as antipsychotics. *The Journal of Pharmacology and Experimental Therapeutics*, 299(1):268-276.

Whitmore, et al. 1942. Abnormal Grignard reactions. XII. Sterically hindered aliphatic carbonyl compounds. II. Ketones containing the dineopentylcarbinyl group. *J. Am. Chem. Soc.*, 64:1247-1251.

Whitmore, et al. 1947. Higher hydrocarbons. IV. Six phenyleicosanes and six cyclohexyleicosanes. *J. Am. Chem. Soc.*, 69:235-237.

Wolf, V. V. 1952. Über alkin-amine I. Aryl-propargyl-amine. *Liebigs Ann. Chem.*, 576:35-45.

Wolfe, et al. 1996. An improved catalyst system for aromatic carbon-nitrogen bond formation: The possible involvement of bis(phosphine) palladium complexes as key intermediates. *J. Am. Chem. Soc.*, 118:7215-7216.

Yamada, et al. 1998. Alternative synthesis of TTF donors with a dioxolane ring, and synthesis of their dithiolane and oxathiolane analogues. *Tetrahedron Letters*, 39:7709-7712.

Yang, et al. 1999. Palladium-catalyzed amination of aryl halides and sulfonates. *Journal of Organometallic Chemistry*, 576:125-146.

Yasuhara, et al. 2000. An activated phosphate for an efficient amide and peptide coupling reagent. *J. Chem. Soc., Perkin Trans. 1*, 17:2901-2902.

Yin, et al. 2002. Pd-catalyzed intermolecular amidation of aryl halides: The discovery that xantphos can be trans-chelating in a palladium complex. *J. Am. Chem. Soc.*, 124:6043-6048.

Yoshida, et al. 1998. Marked improvement of tardive dystonia after replacing haloperidol with risperidone in a schizophrenic patient. *Clinical Neuropharmacology*, 21(1):68-69.

Notice of Allowance and Fee(s) Due and Notice of Allowability dated May 15, 1997, from U.S. Appl. No. 08/273,669, filed Jul. 12, 1994, now U.S. Pat. No. 5,707,798.

Office Action dated Mar. 27, 1998, from U.S. Appl. No. 08/954,724, filed Oct. 20, 1997, now U.S. Pat. No. 5,912,132.

Office Action dated Sep. 14, 1998, from U.S. Appl. No. 08/965,947, filed Nov. 7, 1997, now U.S. Pat. No. 5,955,281.

Interview Summary dated Nov. 17, 1998, from U.S. Appl. No. 08/965,947, filed Nov. 7, 1997, now U.S. Pat. No. 5,955,281.

Notice of Allowance and Fee(s) Due and Notice of Allowability dated Sep. 4, 1998, from U.S. Appl. No. 08/954,724, filed Oct. 20, 1997, now U.S. Pat. No. 5,912,132.

Office Action dated Feb. 28, 2001, from U.S. Appl. No. 09/413,626, filed Oct. 6, 1999, now U.S. Pat. No. 6,358,698.

International Search Report dated Jul. 17, 2001 for PCT/US01/07187.

Notice of Allowance and Fee(s) Due and Notice of Allowability dated Nov. 20, 2001, from U.S. Appl. No. 09/413,626, filed Oct. 6, 1999, now U.S. Pat. No. 6,358,698.

Office Action dated Apr. 25, 2002, from U.S. Appl. No. 09/800,096, now U.S. Pat. No. 6,815,458.

Written Opinion dated Nov. 22, 2002 for PCT/US01/07187.

Office Action dated Jan. 21, 2003, from U.S. Appl. No. 09/800,096, now U.S. Pat. No. 6,815,458.

International Preliminary Examination Report dated Mar. 18, 2003, for PCT/US01/07187.

International Search Report dated May 8, 2003 for PCT/US02/41476.

Notice of Allowance and Fee(s) Due and Notice of Allowability dated Dec. 5, 2003, from U.S. Appl. No. 10/409,782, filed Apr. 7, 2003, now U.S. Pat. No. 6,756,393.

Office Action dated Jul. 15, 2003, from U.S. Appl. No. 09/800,096, now U.S. Pat. No. 6,815,458.

Written Opinion dated Sep. 9, 2003, for PCT/US02/41476.

International Search Report for PCT/US03/19797 dated Dec. 3, 2003.

Notice of Allowability dated Dec. 8, 2003, from U.S. Appl. No. 09/800,096, filed Mar. 6, 2001, now U.S. Pat. No. 6,815,458.

Office Action dated May 21, 2004, from U.S. Appl. No. 10/329,719, filed Dec. 23, 2002, now U.S. Pat. No. 6,911,452.

Office Action dated Nov. 4, 2004, from U.S. Appl. No. 10/601,070, filed Jun. 20, 2003.

International Preliminary Examination Report dated Jan. 15, 2004, for PCT/US02/41476.

Written Opinion for PCT/US03/19797 dated Apr. 5, 2004.

International Preliminary Report on Patentability for PCT/US2004/001234 dated Apr. 14, 2005.

International Preliminary Examination Report for PCT/US03/19797 dated Jul. 28, 2004.

International Search Report for PCT/US2004/001234 dated Sep. 8, 2004.

International Written Opinion for PCT/US2004/001234 dated Sep. 8, 2004.

Office Action dated Jan. 17, 2006, from U.S. Appl. No. 11/154,083, filed Jun. 26, 2005.

Notice of Allowance and Fee(s) Due and Notice of Allowability dated Mar. 29, 2006, from U.S. Appl. No. 10/601,070, filed Jun. 20, 2003.

International Search Report dated Sep. 29, 2005, for PCT/US2005/17808.

International Search Report dated Jan. 30, 2006, for PCT/US2005/034813.

Written Opinion of the International Searching Authority dated Jan. 30, 2006, for PCT/US2005/034813.

International Search Report dated Jan. 30, 2006, for PCT/US2005/034376.

Written Opinion of the International Searching Authority dated Jan. 30, 2006, for PCT/US2005/034376.

Office Action dated Jun. 26, 2006, from U.S. Appl. No. 11/154,083, filed Jun. 26, 2005.

Office Action dated Oct. 5, 2006, from U.S. Appl. No. 11/418,322, filed May 3, 2006.

Office Action dated Jan. 23, 2007, from U.S. Appl. No. 11/418,322, filed May 3, 2006.

Office Action dated Feb. 5, 2007, from U.S. Appl. No. 11/299,566, filed Dec. 12, 2005.

Notice of Allowability, Notice of Allowance and Fee(s) Due, and Interview Summary dated Dec. 15, 2006, from U.S. Appl. No. 11/154,083, filed Jun. 16, 2005.

International Preliminary Report on Patentability dated Mar. 27, 2007, for PCT/US2005/034376.

International Preliminary Report on Patentability dated Mar. 27, 2007, for PCT/US2005/034813.

Office Action dated Apr. 6, 2007, from U.S. Appl. No. 11/418,322, filed May 3, 2006.

Office Action dated May 8, 2007, from U.S. Appl. No. 11/417,866, filed May 3, 2006.

Notice of Allowance and Fee(s) Due and Notice of Allowability dated Jun. 19, 2007, from U.S. Appl. No. 11/418,322, filed May 3, 2006.

U.S.P.T.O. Non-Final Office Action dated Jul. 11, 2008, in U.S. Appl. No. 10/759,561, filed Jan. 15, 2004.

U.S.P.T.O. Non-Final Office Action dated Jan. 6, 2009, in U.S. Appl. No. 10/759,561, filed Jan. 15, 2004.

Official communication in European Patent Application No. 04702584.6-2123, dated Apr. 5, 2006.

Official communication in European Patent Application No. 04702584.6-2123, dated Feb. 23, 2007.

ACADIA Pharmaceuticals Announces Results from Phase III Trial of Pimavanserin in Parkinson's Disease Psychosis ACADIA Pharmaceuticals Announces Results from Phase III Trial of Pimavanserin in Parkinson's Disease Psychosis, *Press Release* (*Business Wire*, San Diego), Sep. 1, 2009.

ACADIA Pharmaceuticals Provide Update on Pimavanserin Collaborative Development Program, *Press Release* (*Business Wire*, San Diego), Oct. 6, 2009.

Marek et al., "Synergistic Action of 5-HT 2A Antagonists and Selective Serotonin Reuptake Inhibitors in Neuropsychiatric Disorders," *Neuropsychopharmacology*, 2003, 28: 402-412.

Benfield, et al. 1986. "Fluoxetine. A review of its pharmacodynamic & pharmacokinetic properties, & therapeutic efficacy in depressive illness," *Drugs*, 32(6):491-508.

Bond et al. 1995. "Physiological effects of inverse agonists in transgenic mice with myocardial overexpression of the $\beta_2$-adrenoceptor," *Nature*, 374:272-276.

Cox, R., 2002. Medicinal Chemistry—$28^{th}$ International Symposium: Jun. 8-12, 2002, San Diego, CA, USA, *IDrugs*, 5(7):626-632.

Dorwald, F.Z., "Side Reactions in Organic Synthesis: A Guide to Successful Synthesis Design" 2005 Wiley-VCH GmbH & KGaA, Wienheim.

Gillman, P. K. 2005. "Monoamine oxidase inhibitors, opioid analgesics and serotonin toxicity," *British Journal of Anaesthesia*, 95(4):434-441.

Glennon, R. A. 1990. "Serotonin receptors: Clinical implications," *Neuroscience & Biobehavioral Reviews*, 14:35-47.

Goodman & Gilman's, *The Pharmacological Basis of Therapeutics*, $7^{th}$ edition, pp. 340-343 & 403-404, 1985.

Gstach et al. 1990. "Rearrangement of 3,3-disubstituted 1-aryl-4,5-dihydro-5-oxo-3*H*-1,2,4-triazolium tetraflluoroborates; Part 1. A versatile synthesis of 1,5-disubstituted 2-aryl-1,2-dihydro-3*H*-1,2,4-triazol-3-one tetrafluoroborates," *Synthesis*, pp. 803-808.

Guthrie, et al. 1993. "The tetrahedral intermediate from the hydration of *N*-methylformanilide," *Can. J. Chem.*, 71:2109-2122.

Harper, et al. 1964. "The chemistry and pharmacology of some 4-aminopiperidines and their derivatives," *J. Med. Chem.*, 44:729-732.

Hartwig, J. F. 1998. "Transition metal catalyzed synthesis of arylamines and aryl ethers from aryl halides and triflates: Scope and mechanism," *Angew. Chem. Int. Ed.*, 37:2047-2067.

Herrick-Davis, et al. 2000. "Inverse agonist activity of atypical antipsychotic drugs at human 5-hydroxytryptamine2C receptors," *The Journal of Pharmacology and Experimental Therapeutics*, 295(1):226-232.

Hickinbottom, W. J. 1930. "The preparation of secondary alkylarylamines and their purification," *J. Chem. Soc.*, pp. 992-994.

Hirst, et al. 1895. "A method for preparing the formyl derivatives of the aromatic amines," *J. Chem. Soc.*, 67:829-831.

Idzikowski, et al. 1991. "A dose response study examining the effects of ritanserin on human slow wave sleep," *Br. J. Clin. Pharmac.*, 31:193-196.

Jaeger, et al. 1941. "Two ketones of the stilboestrol group," *J. Chem. Soc.*, 744-747.

Johnston, et al. 2006. "Drugs in Development for Parkinson's Disease: An Update," *Current Opin. Investig. Drugs*, 7(1):25-32.

Julius, et al. 1990. "The 5HT2 receptor defines a family of structurally distinct but functionally conserved serotonin receptors," *Proc. Natl. Acad. Sci. USA*, 87:928-932.

Kalgutkar, et al. 1995. "Selective inhibitors of monoamine oxidase (MAO-A and MAO-B) as probes of its catalytic site and mechanism," *Medicinal Research Reviews*, 15(4)325-388. XP002034298.

Kanayama, et al. 2005. "New treatment of lumbar disc herniation involving 5-hydroxytryptamine$_{2A}$ receptor inhibitor: A randomized controlled trial," *J. Neurosurg: Spine*, 2:441-446.

Klapars, et al. 2001. "A general and efficient copper catalyst for the amidation of aryl halides and the *N*-arylation of nitrogen heterocycles," *J. Am. Chem. Soc.*, 123:7727-7729.

Klapars, et al. 2002. "A general and efficient copper catalyst for the amidation of aryl halides," *J. Am. Chem. Soc.*, 124:7421-7428.

Kuehne, et al. 1991(a). "Enantioselective syntheses of vinblastine, leurosidine, vincovaline, and 20'-*epi*-vincovaline," *J. Org. Chem.*, 56(2):513-528.

Kuehne, et al. 1991(b). "Total syntheses of *Yohimbe* alkaloids, with stereoselection for the normal, allo, and 3-epiallo series, based on annelations of 4-methoxy-1,2-dihydropyridones," *J. Org. Chem.*, 56(8):2701-2712.

Kwong, et al. 2002(a). "Copper-catalyzed coupling of alkylamines and aryl iodides: An efficient system even in an air atmosphere," *Organic Letters*, 4(4):581-584.

Kwong, et al. 2002(b). "A general, efficient, and inexpensive catalyst system for the coupling of aryl iodides and thiols," *Organic Letters*, 4(20):3517-3520.

Kwong, et al. 2003. "Mild and efficient copper-catalyzed amination of aryl bromides and primary alkylamines," *Organic Letters*, 5(6):793-796.

Landini, et al. 1974. "A convenient synthesis of primary and secondary dialkyl and aryl alkyl sulfides in the presence of phase-transfer catalysts," *Synthesis*, pp. 565-566.

Landolt, et al. 1999. "Serotonin-2 receptors and human sleep: Effect of a selective antagonist on EEG power spectra," *Neuropsychopharmacology*, 21(3):455-466.

Leysen, et al. 1978. "Serotonergic component of neuroleptic receptors," *Nature*, 272:168-171.

Li, G. Y. 2002. "Highly active, air-stable palladium catalysts for the C-C and C-S bond-forming reactions of vinyl and aryl cholrides: Use of commercially available $[(t\text{-Bu})_2P(OH)]_2PdCl_2$, $[(t\text{-Bu})_2P(OH)PdCl_2]_2$, and $[[(t\text{-Bu})_2PO \ldots H \ldots OP(t\text{-Bu})_2]PdCl]_2$ as catalysts," *J. Org. Chem.*, 67:3643-3650.

Liechti, et al. 2001. "Effects of MDMA (ecstasy) on prepulse inhibition and habituation of startle in humans after pretreament with Citalopram, Haloperidol, or Ketanserin," *Neuropsychopharmacology*, 24(3):240-252.

Linder, et al. 1997. "Pharmacogenetics: A laboratory tool for optimizing therapeutic efficiency," *Clinical Chemistry*, 43(2):254-266.

Lowe, et al. 1994. "Aza-tricyclic substance P antagonists," *J. Med. Chem.*, 37:2831-2840.

Mansbach, et al. 1988. "Dopaminergic stimulation disrupts sensorimotor gating in the rat," *Psychopharmacology*, 94:507-514.

March et al., *Journal of Advanced Organic Chemistry: Reactions, Mechanism and Structure*, 5th Edition, p. 423, 2001.

Marek, et al. 2003. "Synergistic action of 5-HT$_{2A}$ antagonists and selective serotonin reuptake inhibitors in neuropsychiatric disorders," *Neuropsychopharmacology*, 28:402-412.

Marek, et al. 2005. "The selective 5-HT$_{2A}$ receptor antagonist M100907 enhances antidepressant-like behavioral effects of the SSRI fluoxetine," *Neuropsychopharmacology*, 30:2205-2215.

Mavunkel, et al. 1996. "Synthesis and characterization of pseudopeptide bradykinin B2 receptor antagonists containing the 1,3,8-triazaspiro[4.5]decan-4-one ring system," *J. Med. Chem.*, 39:3169-3173.

Mayer, et al. 2003. "Ritanserin improves sleep quality in narcolepsy," *Pharmacopsychiatry*, 364:150-155.

Meltzer, et al. 1995. "Plasma clozapine levels and the treatment of L-DOPA-induced psychosis in Parkinson's disease," *Neuropsychopharmacology*, 12(1):39-45.

Meltzer, H. Y. 1999. "The role of serotonin in antipsychotic drug action," *Neuropsychopharmacology*, 21(2S):106S-115S.

Meng, et al. 1991. "Synthetic approaches toward glidobamine, the core structure of the glidobactin antibiotics," *Tetrahedron*, 47(32):62510-6264.

Micovic, et al. 1991. "A simple method for preparation of secondary aromatic amines," *Synthesis*, 11:1043-1045.

Miyata, et al. 2000. "Sarpogrelate, a selective 5-HT$_{2A}$ serotonergic receptor antagonist, inhibits serotonin-induced coronary artery spasm in a porcine model," *Journal of Cardiovascular Pharmacology*, 35(2) 294-301.

Möehrle, et al. 1990. "Sodium mercury edetate dehydrogenation of N-aliphatic substituted 1,2,3,6-tetrahydropyridine derivatives," *Arch. Pharm. (Weinheim)*, 323:109-115.

Moulignier, A. 1994. "Récepteurs centraux de la sérotonine principaux aspects fondamentaux et fonctionnels application thérapeutiques," *Rev. Neurol.*, 150:3-15.

Moune, et al. 1997. "Total synthesis of dolatrienoic acid: A subunit of dolastatin 14," *J. Org. Chem.*, 62:3332-3339.

Mullen et al. 2000. "(−)-Spiro[1-azabicyclo[2.2.2]octane-3,5'-oxazolidin-2'one], a conformationally restricted analogue of acetylcholine, is a highly selective full agonist at the α7 nicotinic acetylcholine receptor," *J. Med. Chem.*, 43:4045-4050.

Muri, et al. 1998. "Synthesis of new benzylic ethers of oximes derived from 1-phenyl-pyrazole compounds," *Synthetic Communications*, 28(7):1299-1321.

Ng, et al. 1970. "L-dopa-induced release of cerebral monoamines," *Science*, 170:76-77.

Nigam, et al. 1957a. "Studies with acetylenes. Part II. Some reactions of Grignard reagents with propargylic halides. Model linoleic and linolenic acid systems," *J. Chem Soc.*, pp. 3868-3873.

Nigam, et al. 1957b. "The conversion of fatty acids into aldehydes," *J. Chem. Soc.*, pp. 3320-3321.

Nordstrom, et al. 1993. "High 5-HT$_2$ receptor occupancy in clozapine treated patients demonstrated by PET," *Psychopharmacology*, 110:365-367.

Ogawa, et al. 2005. "Effects of R-102444 and its active metabolite R-96544, selective 5-HT2A receptor antagonists, on experimental acute and chronic pancreatitis: Additional evidence for possible involvement of 5-HT2A receptors in the development of experimental pancreatitis," *European Journal of Pharmacology*, 521:156-163.

Olah, et al. 1956. "Notiz über die *n*-formylierung von aminen mit formylfluorid," *Chem. Ber.*, 89:2211-2212.

Old, et al. 2002."Efficient palladium-catalyzed *n*-arylation of indoles," *Organic Letters*, 2(10):1403-1406.

Pace, et al. 1991. "A mutant α subunit of $G_{i2}$ induces neoplastic transformation of Rat-1 cells," *Proc. Natl. Acad. Sci. USA*, vol. 88:7031-7035.

Paiva, et al. 1988. "Effects of ritanserin on sleep disturbances of dysthymic patients," *Psychopharmacology*, 96:395-399.

Patel, et al. 2004. "The highly selective 5-hydroxytryptamine (5-HT)$_{2A}$ receptor antagonist, EMD 281014, significantly increases swimming and decreases immobility in male congenital learned helpless rats in the forced swim test," *Synapse*, 52:73-75.

Pierce, et al. 1995. "5-hydroxytryptamine-induced synovial plasma extravasation is mediated via 5-hydroxytryptamine2A receptors on sympathetic efferent terminals," *The Journal of Pharmacology and Experimental Therapeutics*, 275(1):502-508.

Pollak, et al. 1999. "Clozapine in drug-induced psychosis in Parkinson's disease," *The Lancet*, 353:2041-2042.

R & D Focus Drug News, Jan. 24, 2000. Pimvanserin ACADIA lead compounds identified.

R & D Focus Drug News, Nov. 12, 2001. Pimvanserin ACADIA preclinical data.

Read, W. T. 1922. "Researches on hydantoins. Synthesis of the soporific, 4,4-phenylethyl-hydantoin(nirvanol)," *J. Am. Chem. Soc.*, 44:1746-1755.

Ricci, A. 2000. *Modern Amination Methods*. New York: Wiley-VCH.

Rice, et al. 1955. "Raney nickel catalyzed n-alkylation of aniline and benzidine with alcohols," *J. Am. Chem. Soc.*, 77:4052-4054.

Ryckmans, et al. 2002. "First dual NK1 antagonists—serotonin reuptake inhibitors: synthesis and SAR of a new class of potential antidepressants," *Bioorganic & Medicinal Chemistry Letters* 12:261-264.

Sadzot, et al. 1989. "Hallucinogenic drug interactions at human brain 5-HT$_2$ receptors: Implications for treating LSD-induced hallucinogenesis," *Psychopharmacology*, 98:495-499.

Saltzman, et al. 1991. "Cloning of the human serotonin 5-HT2 and 5-HT1C receptor subtypes," *Biochemical and Biophysical Research Communications*, 181(3):1469-1478.

Saxena, et al. 1990. "Cardiovascular effects of serotonin agonists and antagonists," *Journal of Cardiovascular Pharmacology*, 15(Supp. 7):S17-S34.

Scheibye, et al. 1978. "Studies on organophosphorus compounds XXI. The dimer of *p*-methoxyphenylthionophosphine sulfide as thiation reagent. A new route to thiocarboxamides," *Bull. Soc. Chim. Belg.*, 87:229-238.

Schins, et al. 2003. "Increased coronary events in depressed cardiovascular patients: 5-HT$_{2A}$ receptor as missing link?," *Psychosomatic Medicine*, 65:729-737.

Screttas, et al. 1978. "Hydrolithiation of α-olefins by a regiospecific two-step process. Transformation of alkyl phenyl sulfides to alkyllithium reagents," *J. Org. Chem.*, 43(6):1064-1071.

Sharpley, et al. 1994. "Slow wave sleep in humans: Role of 5-HT$_{2A}$ and 5-HT$_{2C}$ receptors," *Neuropharmacology*, 33(3/4):467-471.

Smith, et al. 1995. "New spiropiperdines as potent and selective non-peptide tachykinin NK$_2$ receptor antagonists," *J. Med. Chem.*, 38(19):3772-3779.

Stefancich, et al. 1984. "Agenti antiinfiammatori non-steroidei: Nota III—sintesi ed attività analgesica-antiinfiammatoria di 4-(pirrol-1-il)-fenilacetamidi e di 4-(pirrol-1-il)fenetilamine," *Farmaco Ed. Sci.*, 39(9):752-764.

Stryjer, et al. 2003. "Treatment of neuroleptic-induced akathisia with the 5-HT$_{2A}$ antagonist trazodone," *Clinical Neuropharmacology*, 26(3):137-141.

Thomas, et al. 1997. "Rapid in-plate generation of benzimidazole libraries and amide formation using EEDQ," *Tetrahedron Lett.* 39(29):5099-5102.

Tsukamoto, et al. 1995. "Synthesis and structure-activity studies of a series of 1-oxa-2,8-diazaspiro[4.5]decan-3-ones and related compounds as $M_1$ muscarinic agonists," *Chem. Pharm. Bull.*, 43(9):1523-1529.

Vallar, et al. 1987. "Altered $G_S$ and adenylate cyclase activity in human GH-secreting pituitary adenomas," *Nature*, 330:566-568.

Van Laar, et al. 2001. "Subchronic effects of the GABA-agonist lorazepam and the 5-HT$_{2A/2C}$ antagonist ritanserin on driving performance, slow wave sleep and daytime sleepiness in healthy volunteers," *Psychopharmacology*, 154:189-197.

Varma, et al. 1999. "Microwave-accelerated solvent-free synthesis of thioketones, thiolactones, thioamides, thionoesters, and thioflavonoids," *Organic Letters*, 1(5):697-700.

Viola, et al. 2002. "Ritanserin, a serotonin-2 receptor antagonist, improves ultradian sleep rhythmicity in young poor sleepers," *Clinical Neurophysiology*, 113:429-434.

Vogel, A. I. 1948. "Physical properties and chemical constitution. Part XIX. Five-membered and six-membered carbon rings," *J. Chem. Soc.*, pp. 1809-1813.

Vogl, et al. 2002. "Palladium-catalyzed monoarylation of nitroalkanes," *J. Org. Chem.*, 67(1):106-111.

Wade, et al. 2000. "Application of base cleavable safety catch linkers to solid phase library production," *J. Comb. Chem.*, 2(3):266-275.

Weiner, et al. 2001. "5-Hydroxytryptamine$_{2A}$ receptor inverse agonists as antipsychotics," *The Journal of Pharmacology and Experimental Therapeutics*, 299(1):268-276.

Whitmore, et al. 1942. "Abnormal Grignard reactions. XII. Sterically hindered aliphatic carbonyl compounds. II. Ketones containing the dineopentylcarbinyl group," *J. Am. Chem. Soc.*, 64:1247-1251.

Whitmore, et al. 1947. "Higher hydrocarbons. IV. Six phenyleicosanes and six cyclohexyleicosanes," *J. Am. Chem. Soc.*, 69:235-237.

Wolfe, et al. 1996. "An improved catalyst system for aromatic carbon-nitrogen bond formation: The possible involvement of bis(phosphine) palladium complexes as key intermediates," *J. Am. Chem. Soc.*, 118:7215-7216.

Yamada, et al. 1998. "Alternative synthesis of TTF donors with a dioxolane ring, and synthesis of their dithiolane and oxathiolane analogues," *Tetrahedron Letters*, 39:7709-7712.

Yang, et al. 1999. "Palladium-catalyzed amination of aryl halides and sulfonates," *Journal of Organometallic Chemistry*, 576:125-146.

Yasuhara, et al. 2000. "An activated phosphate for an efficient amide and peptide coupling reagent," *J. Chem. Soc., Perkin Trans. 1*, 17:2901-2902.

Yin, et al. 2002. "Pd-catalyzed intermolecular amidation of aryl halides: The discovery that xantphos can be trans-chelating in a palladium complex," *J. Am. Chem. Soc.*, 124:6043-6048.

Yoshida, et al. 1998. "Marked improvement of tardive dystonia after replacing haloperidol with risperidone in a schizophrenic patient," *Clinical Neuropharmacology*, 21(1):68-69.

Office Action dated May 21, 2004, from U.S. Appl. No. 10/329,719, filed Dec. 23, 2002, now U.S. Pat. No. 6,911,452.

Notice of Allowance and Fee(s) Due and Notice of Allowability dated Feb. 11, 2005, from U.S. Appl. No. 10/329,719 filed Dec. 23, 2002, now U.S. Pat. No. 6,911,452.

Notice of Allowance and Fee(s) Due and Notice of Allowability dated Jul. 12, 2005, from U.S. Appl. No. 10/601,070, filed Jun. 20, 2003.
International Search Report dated Dec. 3, 2003, for PCT/US03/19797.
International Preliminary Examination Report dated Jul. 28, 2004 for PCT/US03/19797.
International Search Report dated Sep. 8, 2004, for PCT/US2004/001234.
International Written Opinion dated Sep. 8, 2004, for PCT/US2004/001234.
Written Opinion mailed on Dec. 15, 2004.
International Preliminary Report on Patentability dated Apr. 14, 2005, for PCT/US2004/001234.
Notice of Allowance and Fee(s) Due and Notice of Allowability dated Mar. 5, 2007, from U.S. Appl. No. 10/601,070, filed Jun. 20, 2003.
Office Action dated Oct. 22, 2007 from U.S. Appl. No. 11/417,782, filed May 3, 2006.
Office Action dated Oct. 12, 2007 from U.S. Appl. No. 11/417,439, filed May 3, 2006.
Office Action dated Oct. 2, 2007, from U.S. Appl. No. 11/299,566, filed Dec. 12, 2005.
Office Action dated Oct. 26, 2007, from U.S. Appl. No. 11/417,866, filed May 3, 2006.
Office Action dated Oct. 10, 2007, from U.S. Appl. No. 10/759,561, filed Jan. 15, 2004.
Office Action dated Jan. 30, 2008, from U.S. Appl. No. 11/417,790, filed May 3, 2006.
Office Action dated Jan. 25, 2008, from U.S. Appl. No. 10/802,970, filed Mar. 16, 2004.
Notice of Allowance and Fee(s) Due and Notice of Allowability dated Feb. 19, 2008, from U.S. Appl. No. 11/417,439, filed May 3, 2006.
Office Action dated Dec. 17, 2007, from U.S. Appl. No. 11/299,566, filed Dec. 12, 2005.
Office Action dated Feb. 22, 2008, from U.S. Appl. No. 11,417,866, filed May 3, 2006.
Office Action dated Mar. 28, 2008, from U.S. Appl. No. 11/417,782, filed May 3, 2006.
Office Action dated Jul. 14, 2006, from U.S. Appl. No. 10/601,070, filed Jun. 20, 2003.
Supplemental Notice of Allowability dated May 23, 2008, from U.S. Appl. No. 11/417,439, filed May 3, 2006.
Office Action dated Jun. 2, 2008, from U.S. Appl. No. 11/687,552, filed Mar. 16, 2007.
Office Action dated Jul. 17, 2008, from U.S. Appl. No. 10/802,970, filed Mar. 16, 2004.
Notice of Allowance and Fee(s) Due and Notice of Allowability dated Jul. 23, 2008, from U.S. Appl. No. 11/299,566, filed Dec. 12, 2005.
Maubach, K., "Psychiatric Drug Discovery and Development," *Expert Opin. Investig. Drugs.*, vol. 12, No. 9, 1571-1575 (2003).
Meltzer et al., "Serotonin Receptors: Their Key Role in Drugs to Treat Schizophrenia," *Progress in Neuro-Pyschopharmacology & Biol. Psych.*, vol. 27, pp. 1159-1172 (2003).
Morgan et al., "Emerging Drugs for Parkinson's Disease," *Expert Opin. Emerging Drugs.*, vol. 11, No. 3, pp. 403-417 (2006).
Roberts, C. "Drug Evaluation: ACP-103, a 5-HT2A Receptor Inverse Agonist," *Current Opin. Investig. Drugs*, vol. 7, No. 7, pp. 653-660 (2006).
Scriabine, A., "Psychiatric Drug Discovery and Development," *CNS Drug Rev.*, vol. 9, No. 3, pp. 319-326 (2003).
Vanover et al., "ACP-103, A 5-HT2A Receptor Inverse Agonist, A Novel Potential Treatment For Psychosis," *Schizophrenia Research*, vol. 60, No. 1, Supp. [S], p. 317 (2003).
Vanover et al., "ACP-103, A 5-HT2A Receptor Inverse Agonist: Safety, Tolerability and Pharmacokinetics in Healthy Volunteers," *International J. Neuropsychopharmacology*, vol. 7, No. Supp. 2, pp. S253 (2004).
Vanover et al., "Pharmacological Characterization of AC-90179 [2-(4-Methoxy-phenyl)-*N*-(4-methyl-benzyl)-*N*-(1-methyl-piperidiny-4-yl)-acetamide Hydrochloride]: A Selective Serotonin 2A Receptor Inverse Agonist," *J. Pharmacology & Experimental Therapeutics*, vol. 310, No. 3, pp. 943-951 (2004).
Vanover et al., "Pharmacological and Behavioral Profile of *N*-(4-fluorophenylmethyl)-*N*-(1-methylpiperidin'4-yl)-*N'*-(4-(2-methylpropyloxy)phenylmethyl) Carbamide (2*R*, 3*R*)-Dihydroxybutanedioate (2:1) (ACP-103), a Novel 5-Hydroxytrptamine 2A Receptor Inverse Agonist," *J. Pharmacology & Experimental Therapeutics*, vol. 317, No. 2, pp. 910-918 (2006).
Office Action dated Aug. 22, 2007 in U.S. Appl. No. 11/122,293, filed May 4, 2005.

* cited by examiner

SELECTIVE SEROTONIN RECEPTOR INVERSE AGONISTS AS THERAPEUTICS FOR DISEASE

BACKGROUND OF THE INVENTION

1. Field of the Invention

The present invention relates to novel combinations of compounds that are effective as therapeutic agents in the treatment of depression, mania, or social phobia, and other psychotic disorders. The combinations include inverse serotonin agonists and another antidepressant, anti-maniac, anti-phobia, or antipsychotic agent.

2. Description of the Related Art

Serotonin or 5-hydroxytryptamine (5-HT) plays a significant role in the functioning of the mammalian body. In the central nervous system, 5-HT is an important neurotransmitter and neuromodulator that is implicated in such diverse behaviors and responses as sleeping, eating, locomotion, perceiving pain, learning and memory, sexual behavior, controlling body temperature and blood pressure. In the spinal column, serotonin plays an important role in the control systems of the afferent peripheral nociceptors (Moulignier, Rev. Neurol. 150:3-15, (1994)). Peripheral functions in the cardiovascular, hematological and gastrointestinal systems have also been ascribed to 5-HT. 5-HT has been found to mediate a variety of contractile, secretory, and electrophysiologic effects including vascular and nonvascular smooth muscle contraction, and platelet aggregation. (Fuller, *Biology of Serotonergic Transmission,* 1982; Boullin, *Serotonin In Mental Abnormalities* 1:316 (1978); Barchas, et al., *Serotonin and Behavior,* (1973)). The 5-HT2A receptor subtype (also referered to as subclass) is widely yet discretely expressed in the human brain, including many cortical, limbic, and forebrain regions postulated to be involved in the modulation of higher cognitive and affective functions. This receptor subtype is also expressed on mature platelets where it mediates, in part, platelet aggregation, one of the initial steps in the process of vascular thrombosis.

Given the broad distribution of serotonin within the body, it is understandable that tremendous interest in drugs that affect serotonergic systems exists (Gershon, et al., *The Peripheral Actions of 5-Hydroxytryptamine,* 246 (1989); Saxena, et al., *J. Cardiovascular Pharmacol.* 15: Supp. 7 (1990)). Serotonin receptors are members of a large human gene family of membrane-spanning proteins that function as transducers of intercellular communication. They exist on the surface of various cell types, including neurons and platelets, where, upon their activation by either their endogenous ligand serotonin or exogenously administered drugs, they change their conformational structure and subsequently interact with downstream mediators of cellular signaling. Many of these receptors, including the 5-HT2A subclass, are G-protein coupled receptors (GPCRs) that signal by activating guanine nucleotide binding proteins (G-proteins), resulting in the generation, or inhibition of, second messenger molecules such as cyclic AMP, inositol phosphates, and diacylglycerol. These second messengers then modulate the function of a variety of intracellular enzymes, including kinases and ion channels, which ultimately affect cellular excitability and function.

At least 15 genetically distinct 5-HT receptor subtypes have been identified and assigned to one of seven families (5-HT1-7). Each subtype displays a unique distribution, preference for various ligands, and functional correlate(s).

Serotonin may be an important component in various types of pathological conditions such as certain psychiatric disorders (depression, aggressiveness, panic attacks, obsessive compulsive disorders, psychosis, schizophrenia, suicidal tendency), certain neurodegenerative disorders (Alzheimer-type dementia, Parkinsonism, Huntington's chorea), anorexia, bulimia, disorders associated with alcoholism, cerebral vascular accidents, and migraine (Meltzer, *Neuropsychopharmacology,* 21:106S-115S (1999); Barnes & Sharp, *Neuropharmacology,* 38:1083-1152 (1999); Glennon, *Neurosci. Biobehavioral Rev.,* 14:35 (1990)). Recent evidence strongly implicates the 5-HT2 receptor subtype in the etiology of such medical conditions as hypertension, thrombosis, migraine, vasospasm, ischemia, depression, anxiety, psychosis, schizophrenia, sleep disorders and appetite disorders.

Schizophrenia is a particularly devastating neuropsychiatric disorder that affects approximately 1% of the human population. It has been estimated that the total financial cost for the diagnosis, treatment, and lost societal productivity of individuals affected by this disease exceeds 2% of the gross national product (GNP) of the United States. Current treatment primarily involves pharmacotherapy with a class of drugs known as antipsychotics. Antipsychotics are effective in ameliorating positive symptoms (e.g., hallucinations and delusions), yet they frequently do not improve negative symptoms (e.g., social and emotional withdrawal, apathy, and poverty of speech).

Currently, nine major classes of antipsychotics are prescribed to treat psychotic symptoms. Use of these compounds is limited, however, by their side effect profiles. Nearly all of the "typical" or older generation compounds have significant adverse effects on human motor function. These "extrapyramidal" side effects, so termed due to their effects on modulatory human motor systems, can be both acute (e.g., dystonic reactions, a potentially life threatening but rare neuroleptic malignant syndrome) and chronic (e.g., akathisias, tremors, and tardive dyskinesia). Drug development efforts have, therefore, focused on newer "atypical" agents free of these adverse effects.

Antipsychotic drugs have been shown to interact with a large number of central monoaminergic neurotransmitter receptors, including dopaminergic, serotonergic, adrenergic, muscarinic, and histaminergic receptors. It is likely that the therapeutic and adverse effects of these drugs are mediated by distinct receptor subtypes. The high degree of genetic and pharmacological homology between these receptor subtypes has hampered the development of subtype-selective compounds, as well as the determination of the normal physiologic or pathophysiologic role of any particular receptor subtype. Thus there is a need to develop drugs that are selective for individual receptor classes and subclasses amongst monoaminergic neurotransmitter receptors.

The prevailing theory for the mechanism of action of antipsychotic drugs involves antagonism of dopamine D2 receptors. Unfortunately, it is likely that antagonism of dopamine D2 receptors also mediates the extrapyramidal side effects. Antagonism of 5-HT2A is an alternate molecular mechanism for drugs with antipsychotic efficacy, possibly through antagonism of heightened or exaggerated signal transduction through serotonergic systems. 5-HT2A antagonists are therefore good candidates for treating psychosis without extrapyramidal side effects.

Traditionally, these receptors have been assumed to exist in a quiescent state unless activated by the binding of an agonist (a drug that activates a receptor). It is now appreciated that many, if not most, of the GPCR monoamine receptors, including serotonin receptors, can exist in a partially activated state in the absence of their endogenous agonists. This increased basal activity (constitutive activity) can be inhibited by compounds called inverse agonists. Both agonists and inverse agonists possess intrinsic activity at a receptor, in that they alone can activate or inactivate these molecules, respectively. In contrast, classic or neutral antagonists compete against agonists and inverse agonists for access to the receptor, but do not possess the intrinsic ability to inhibit elevated basal or constitutive receptor responses.

We have recently elucidated an important aspect of 5-HT2A receptor function by applying the Receptor Selection and Amplification Technology (U.S. Pat. No. 5,707,798, 1998; Chem Abstr. 128:111548 (1998) and citations therein), to the study of the 5-HT2 subclass of serotonin receptors. R-SAT is a phenotypic assay of receptor function that involves the heterologous expression of receptors in mammalian fibroblasts. Using this technology we were able to demonstrate that native 5-HT2A receptors possess significant constitutive, or agonist-independent, receptor activity (U.S. Patent Application Ser. No. 60/103,317, herein incorporated by reference). Furthermore, by directly testing a large number of centrally acting medicinal compounds with known clinical activity in neuropsychiatric disease, we determined that compounds with antipsychotic efficacy all shared a common molecular property. Nearly all of these compounds, which are used by psychiatrists to treat psychosis, were found to be potent 5-HT2A inverse agonists. This unique clinico-pharmacologic correlation at a single receptor subtype is compelling evidence that 5-HT2A receptor inverse agonism is a molecular mechanism of antipsychotic efficacy in humans.

Detailed pharmacological characterization of a large number of antipsychotic compounds revealed that they possess broad activity at multiple related receptor subtypes. Most of these compounds display agonist, competitive antagonist, or inverse agonist activity at multiple monoaminergic receptor subtypes, including serotoninergic, dopaminergic, adrenergic, muscarinic and histaminergic receptors. This broad activity is likely responsible for the sedating, hypotensive, and motor side effects of these compounds. It would therefore be of great advantage to develop compounds that are selective inverse agonists of the 5-HT2A receptor, but which have little or no activity on other monamine receptors subtypes, especially dopamine D2 receptors. Such compounds may be useful in the treatment of human disease (e.g., as anti-psychotics), and may avoid the adverse side effects associated with non-selective receptor interactions.

SUMMARY OF THE INVENTION

Disclosed herein are pharmaceutical compositions comprising an inverse serotonin receptor agonist or a serotonin receptor antagonist and an anti-psychotic agent. Disclosed herein are also methods of treating psychotic disorders using the disclosed pharmaceutical compositions.

DETAILED DESCRIPTION OF THE PREFERRED EMBODIMENT

Definitions

For the purpose of the current disclosure, the following definitions shall in their entireties be used to define technical terms, and shall also, in their entireties, be used to define the scope of the composition of matter for which protection is sought in the claims.

"Constitutive activity" is defined as the elevated basal activity of a receptor that is independent of the presence of an agonist. Constitutive activity of a receptor may be measured using a number of different methods, including cellular (e.g., membrane) preparations (see, e.g., Barr &. Manning, J. Biol. Chem. 272:32979-87 (1997)), purified reconstituted receptors with, or without the associated G-protein in phospholipid vesicles (Cerione et al., Biochemistry 23:4519-25 (1984)), and functional cellular assays (U.S. Patent Application Ser. No. 60/103,317) or any other method known in the art.

"Agonist" is defined as a compound that increases the basal activity of a receptor when it contacts the receptor.

An "antagonist" is defined as a compound that competes with an agonist or inverse agonist for binding to a receptor, thereby blocking the action of an agonist or inverse agonist on the receptor. However, an antagonist (also known as a "neutral" antagonist) has no effect on constitutive receptor activity.

An "inverse agonist" is defined as a compound that decreases the basal activity of a receptor (i.e., signaling mediated by the receptor). Such compounds are also known as negative antagonists. An inverse agonist is a ligand for a receptor that causes the receptor to adopt an inactive state relative to a basal state occurring in the absence of any ligand. Thus, while an antagonist can inhibit the activity of an agonist, an inverse agonist is a ligand that can alter the conformation of the receptor in the absence of an agonist. The concept of an inverse agonist has been explored by Bond et al. in Nature 374:272 (1995). More specifically, Bond et al. have proposed that unliganded $\beta_2$-adrenoceptor exists in an equilibrium between an inactive conformation and a spontaneously active conformation. Agonists are proposed to stabilize the receptor in an active conformation. Conversely, inverse agonists are believed to stabilize an inactive receptor conformation. Thus, while an antagonist manifests its activity by virtue of inhibiting an agonist, an inverse agonist can additionally manifest its activity in the absence of an agonist by inhibiting the spontaneous conversion of an unliganded receptor to an active conformation.

The "5-HT2A receptor" is defined as a receptor, having an activity corresponding to the activity of the human serotonin receptor subtype, which was characterized through molecular cloning and pharmacology as detailed in Saltzman et al., Biochem. Biophys. Res. Comm. 181:1469-78; and Julius et al., Proc. Natl. Acad. Sci. USA 87:928-932, the disclosures of which are incorporated herein by reference in their entireties.

The term "subject" refers to an animal, preferably a mammal, most preferably a human, who is the object of treatment, observation or experiment.

"Selective" is defined as a property of a compound whereby an amount of the compound sufficient to effect a desired response from a particular receptor type, subtype, class or subclass with significantly less or substantially little or no effect upon the activity other receptor types. For example, a selective compound may have at least a 10-fold greater effect on activity of the desired receptor than on other receptor types. In some cases, a selective compound may have at least a 20-fold greater effect on activity of the desired receptor than on other receptor types, or at least a 50-fold greater effect, or at least a 100-fold greater effect, or at least a 1000-fold greater effect, or at least a 10,000-fold greater effect, or at least a 100,000-fold greater effect, or more than a 100,000-fold greater effect. "Selectivity" or "selective," as an inverse agonist is understood as a property of the compound of the invention whereby an amount of compound that effectively inversely agonizes the 5-HT2A receptor, and thereby decreases its activity, causes little or no inverse agonistic or antagonistic activity at other, related or unrelated, receptors. In particular, in one embodiment, a compound has surprisingly been found not to interact strongly with other serotonin receptors (5-HT 1A, 1B, 1D, 1E, 1F, 2B, 2C, 4A, 6, and 7) at concentrations where the signaling of the 5-HT2A receptor is strongly or completely inhibited. In one embodiment, the compound is also selective with respect to other monoamine-binding receptors, such as the dopaminergic, histaminergic, adrenergic and muscarinic receptors. Compounds that are highly selective for 5-HT2A receptors may have a beneficial effect in the treatment of psychosis, schizophrenia or similar neuropsychiatric disorders, while avoiding adverse effects associated with drugs hitherto suggested for this purpose.

Serotonin or 5-hydroxytryptamine (5-HT) plays a significant role in the functioning of the mammalian body. In the central nervous system, 5-HT is an important neurotransmitter and neuromodulator that is implicated in such diverse behaviors and responses as sleeping, eating, locomotion, perceiving pain, learning and memory, sexual behavior, controlling body temperature and blood pressure. In the spinal column, serotonin plays an important role in the control systems of the afferent peripheral nociceptors (Moulignier, Rev. Neurol. 150:3-15, (1994)). Peripheral functions in the cardiovascular, hematological, and gastrointestinal systems have also been ascribed to 5-HT. 5-HT has been found to mediate a variety of contractile, secretory, and electrophysiologic effects including vascular and nonvascular smooth muscle contraction, and platelet aggregation. (Fuller, *Biology of Serotonergic Transmission*, 1982; Botillin, *Serotonin In Mental Abnormalities* 1:316 (1978); Barchas, et al., *Serotonin and Behavior*, (1973)). The 5-HT2A receptor subtype (also referred to as subclass) is widely yet discretely expressed in the human brain, including many cortical, limbic, and forebrain regions postulated to be involved in the modulation of higher cognitive and affective functions. This receptor subtype is also expressed on mature platelets where it mediates, in part, platelet aggregation, one of the initial steps in the process of vascular thrombosis.

Given the broad distribution of serotonin within the body, it is understandable that tremendous interest in drugs that affect serotonergic systems exists (Gershon, et at, *The Peripheral Actions of 5-Hydroxytryptamine*, 246 (1989); Saxena, et at, *J. Cardiovascular Pharmacol.* 15: Supp. 7 (1990)). Serotonin receptors are members of a large human gene family of membrane-spanning proteins that function as transducers of intercellular communication. They exist on the surface of various cell types, including neurons and platelets, where, upon their activation by either their endogenous ligand serotonin or exogenously administered drugs, they change their conformational structure and subsequently interact with downstream mediators of cellular signaling. Many of these receptors, including the 5-HT2A subclass, are G-protein coupled receptors (GPCRs) that signal by activating guanine nucleotide binding proteins (G-proteins), resulting in the generation, or inhibition of, second messenger molecules such as cyclic AMP, inositol phosphates, and diacylglycerol. These second messengers then modulate the function of a variety of intracellular enzymes, including kinases and ion channels, which ultimately affect cellular excitability and function.

At least 15 genetically distinct 5-HT receptor subtypes have been identified and assigned to one of seven families (5-HT1-7). Each subtype displays a unique distribution, preference for various ligands, and functional correlate(s). Serotonin may be an important component in various types of pathological conditions such as certain psychiatric disorders (depression, aggressiveness, panic attacks, obsessive compulsive disorders, psychosis, schizophrenia, suicidal tendency), certain neurodegenerative disorders (Alzheimer-type dementia, Parkinsonism, Huntington's chorea), anorexia, bulimia, disorders associated with alcoholism, cerebral vascular accidents, and migraine (Meltzer, *Neuropsychopharmacology*, 21 :106S-115S (1999); Barnes & Sharp, *Neuropharmacology*, 38:1083-1152 (1999); Glennon, *Neurosci. Biobehavioral Rev.*, 14:35 (1990)). Recent evidence strongly implicates the 5-HT2 receptor subtype in the etiology of such medical conditions as hypertension, thrombosis, migraine, vasospasm, ischemia, depression, anxiety, psychosis, schizophrenia, sleep disorders and appetite disorders.

In one aspect, the present invention relates to a method of treating depression in a patient comprising identifying a patient in need thereof, and administering to the patient a therapeutically effective amount of a first compound in combination with a therapeutically effective amount of a second compound.

In another aspect, the present invention relates to a method of treating mania in a patient comprising identifying a patient in need thereof, and administering to the patient a therapeutically effective amount of a first compound in combination with a therapeutically effective amount of a second compound.

In yet another aspect, the present invention relates to a method of treating social phobia in a patient comprising identifying a patient in need thereof, and administering to the patient a therapeutically effective amount of a first compound in combination with a therapeutically effective amount of a second compound.

In a further aspect, the present invention relates to a method of treating psychosis in a patient comprising identifying a patient in need thereof, and administering to the patient a therapeutically effective amount of a first compound in combination with a therapeutically effective amount of a second compound.

In another aspect, the present invention relates to a method of treating a neuropsychiatric disorder in a patient comprising identifying a patient in need thereof, and administering to said patient a therapeutically effective amount of a first compound in combination with a therapeutically effective amount of a second compound. In some embodiments, the neuropsychiatric disorder is selected from the group consisting of schizophrenia and related idiopathic psychoses, anxiety, sleep disorders, appetite disorders, affective disorders such as major depression, bipolar disorder, and depression with psychotic features, and Tourette's Syndrome, drug-induced psychoses, psychoses secondary to neurodegenerative disorders such Alzheimer's or Huntington's Disease.

The term "therapeutically effective amount" as used herein means an amount of an active compound or pharmaceutical agent that elicits the biological or medicinal response in a tissue, system, animal or human that is being sought by a researcher, veterinarian, medical doctor or other clinician, which includes alleviation, amelioration, or lessening of the symptoms of the disease being treated, or prevents or slows the progress of the disease or increase of the symptoms.

In certain embodiments, the patient may be a mammal. The mammal may be selected from the group consisting of mice, rats, rabbits, guinea pigs, dogs, cats, sheep, goats, cows, primates, such as monkeys, chimpanzees, and apes, and humans. In some embodiments, the patient is a human.

In some embodiments, the first compound in the above methods is an inverse agonist selective for a serotonin receptor. In certain embodiments, the serotonin receptor is a 5HT2A receptor, while in other embodiments the serotonin receptor is a 5HT2C receptor. In other embodiments, the inverse agonists binds to a 5HT2A receptor and a 5HT2C receptor.

In some embodiments, the first compound is a compound of formula (I)

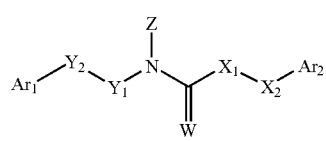

I

-continued

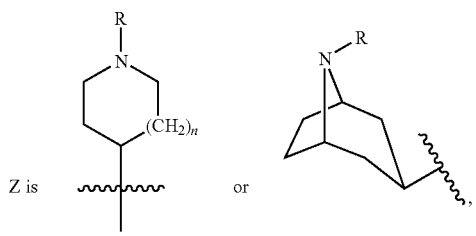

where

Z is wherein R is a hydrogen, a cyclic or straight-chained or branched acyclic organyl group, a lower hydroxyalkyl group, a lower aminoalkyl group, or an aralkyl or heteroaralkyl group; and n is 1;

$X_1$ is methylene, vinylene, or an NH or N(lower alkyl) group; and $X_2$ is methylene; or, when $X_1$ is methylene or vinylene, $X_2$ is methylene or a bond; or when $X_1$ is methylene, $X_2$ is O, S, NH, or N(lower alkyl) or a bond;

$Y_1$ is methylene and $Y_2$ is methylene, vinylene, ethylene, propylene, or a bond; or $Y_1$ is a bond and $Y_2$ is vinylene; or $Y_1$ is ethylene and $Y_2$ is O, S, NH, or N(lower alkyl);

$Ar_1$ and $Ar_2$ independently are unsubstituted or substituted aryl or heteroaryl groups, provided that $Ar_1$ and $Ar_2$ are not simultaneously unsubstituted phenyl; and W is oxygen; or a pharmaceutically acceptable salt or prodrug thereof.

In other embodiments, the first compound is a compound disclosed in U.S. patent application Publication Ser. No. 2002/0004513 A1, published on Jan. 10, 2002, by Andersson et al., and entitled "AZACYCLIC COMPOUNDS," which is the publication of the U.S. application Ser. No. 09/800,096, or in U.S. patent application Publication Ser. No. 2003/0220316 A1, published on Nov. 27, 2003, by Andersson et al., and entitled "AZACYCLIC COMPOUNDS," which is the publication of the U.S. application Ser. No. 10/409,782, or in U.S. application Ser. No. 10/802,970, filed on Mar. 16, 2004, by Andersson et al., and entitled "AZACYCLIC COMPOUNDS," the entire disclosure of all of which is hereby incorporated by reference herein in their entirety, including any drawings.

In another embodiment, the first compound is N-(1-methylpiperidin-4-yl)-N-(4-fluorophenylmethyl)-N'-(4-(2-methylpropyloxy)phenylmethyl)carbamide, which is the

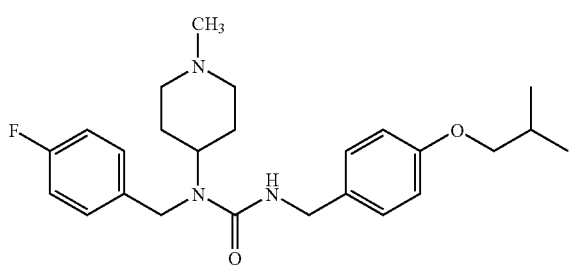

(I)

In another embodiment, the first compound in the above methods is an antagonist selective for a serotonin receptor. In certain embodiments, the serotonin receptor is a 5HT2A receptor, while in other embodiments the serotonin receptor is a 5HT2C receptor. In other embodiments, the antagonists binds to a 5HT2A receptor and a 5HT2C receptor.

In some embodiments, the second compound in the above methods is a selective serotonin reuptake inhibitor (SSRI). Examples of SSRIs include, but are not limited to, bupropion (Wellbutrin, Zyban), citalopram (Celexa), duloxetine, escitalopram (Lexapro), fluoxetine (Prozac), fluvoxamine (Luvox), nefazodone (Serzone), paroxetine (Paxil), sertaline (Zoloft), sibutramine, trazodone (Dividose), and venlafaxine. Any other SSRI currently known or later developed are within the scope of the present disclosure.

In other embodiments, the second compound in the above methods is a serotonin/norepinephrine reuptake inhibitor (SNRI). Examples of SNRIs include, but are not limited to, citalopram (Celexa), dulexetine, escitalopram (Lexapro), fluvoxamine (Luvox), and venfalaxine (effexor). Any other SNRI currently known or later developed are within the scope of the present disclosure.

In further embodiments, the second compound in the above methods is a monoamine oxidase inhibitor (MAO-I). Examples of MAO-Is include, but are not limited to, tranylcypromine (Pamate), phenelzine (Nardil), maprotiline, and isocarboxazid (Marplan). Any other MAO-I currently known or later developed are within the scope of the present disclosure.

In yet other embodiments, the second compound in the above methods is a tricyclic antidepressant (TCA). Examples of TCAs include, but are not limited to, amitryptiline (Norpramine), amoxapineclomipramine (Anafranil), desipramine, doxepin (Sinequan), imipramine (Tofranil), maprotiline, (Elavil), protryptiline, and trimipramine. Any other TCA currently known or later developed are within the scope of the present disclosure.

In some other embodiments, the second compound in the above methods is a compound selected from aripiprazole (Abilify), clozapine, fluoxetine/olanzapine (Symbyax), olanzapine (Zyprexa), quetiapine (Seroquel), risperidone (Risperdal), valproic acid (Depakote), and ziprasidone (Geodon). Any other atypical antidepressant currently known or later developed are within the scope of the present disclosure.

In some embodiments, the second compound in the above methods is a compound selected from chlorpromazine (Thorazine®), mesoridazine (Serentil®), prochlorperazine (Compazine®), thioridazine (Mellaril®), haloperidol (Haldol®), pimozide (Orap®), clozapine (Clozaril®), loxapine (Loxitane®), olanzapine (Zyprexa®), quetiapine (Seroquel®), resperidone (Resperidal®), ziprasidone (Geodon®), lithium carbonate, Aripiprazole (Abilify), Clozapine, Clozaril, Compazine, Etrafon, Geodon, Haldol, Inapsine, Loxitane, Mellaril, Moban, Navane, Olanzapine (Zyprexa), Orap, Permitil, Prolixin, Phenergan, Quetiapine (Seroquel), Reglan, Risperdal, Serentil, Seroquel, Stelazine, Taractan, Thorazine, Triavil, Trilafon, and Zyprexa.

In some embodiments, the second compound in the above methods is an antipsychotic agent. The antipsychotic agent may be selected from the group consisting of a phenothiazine, phenylbutylpiperadine, debenzapine, benzisoxidil, and salt of lithium. The phenothiazine group of compounds may be selected from the group consisting of chlorpromazine (Thorazine®), mesoridazine (Serentil®), prochlorperazine (Compazine®), and thioridazine (Mellaril®). The phenylbutylpiperadine group of compounds may be selected from the group consisting of haloperidol (Haldol®), and pimozide (Orap(®). The debenzapine group of compounds may be selected from the group consisting of clozapine (Clozaril®), loxapine (Loxitane®), olanzapine (Zyprexa®) and quetiapine (Seroquel®). The benzisoxidil group of compounds may be selected from the group consisting of resperidone (Resperidal®) and ziprasidone (Geodon®). The salt of lithium may be lithium carbonate. In some embodiments, the antipsychotic agent may be selected from the group consisting of Aripiprazole (Abilify), Clozapine, Clozaril, Compazine, Etrafon, Geodon, Haldol, Inapsine, Loxitane, Mellaril, Moban, Navane, Olanzapine (Zyprexa), Orap, Permitil, Prolixin, Phenergan, Quetiapine (Seroquel), Reglan, Risperdal, Serentil, Seroquel, Stelazine, Taractan, Thorazine, Triavil, Trilafon, and Zyprexa, or pharmaceutically acceptable salts thereof.

In other embodiments, the second compound in the above methods is a norepinephrine reuptake inhibitor. The norepinephrine reuptake inhibitor is selected from the group consisting of thionisoxetine and reboxetine.

In further embodiments, the second compound in the above methods is a dopamine agonist. The dopamine agonist may be selected from the group consisting of sumatriptan, almotriptan, naratriptan, frovatriptan, rizatriptan, zomitriptan, cabergoline, amantadine, lisuride, pergolide, ropinirole, pramipexole, and bromocriptine.

In yet another embodiment, the second compound in the above methods is an anti-insomnia drug. Examples of anti-insomnia drugs include, but are not limited to, alprazolam (Xanax), chlordiazepoxide (Librium, Limbitrol), clorazepate (Tranxene), estazolam (ProSom), flurazepam (Dalmane), hydroxyzine (Atarax), lorazepam (Ativan), pentobarbital (Nembutal), quazepam (Doral), secobarbital (Seconal), temazepam (Restoril), triazolam (Halcion), valium, zaleplon (Sonata), zolpidem (Ambien), and the benzodiazepine family of drugs. Any other anti-insomnia drug currently known or later developed are within the scope of the present disclosure.

In other embodiments, the second compound in the above methods is an anti-manic drug. Examples of anti-manic drugs include, but are not limited to, divalproex (Depakote), lithium carbonate (Eskalith), and lithium citrate. Any other anti-manic drug currently known or later developed are within the scope of the present disclosure.

In some embodiments, the second compound in the above methods is an anti-phobia drug. An example of anti-phobia drugs includes, but is not limited to, D-cycloserine. Those of skill in the art recognize that some of the other drugs disclosed herein also work as anti-phobia drugs. Any other anti-manic drug currently known or later developed are within the scope of the present disclosure.

In another embodiment, the second compound in the above methods is a serotonin 2A antagonist. Tthe serotonin 2A antagonist may be M 100,907 or an analog thereof. By "M 100,907," it is meant the compound of Formula II.

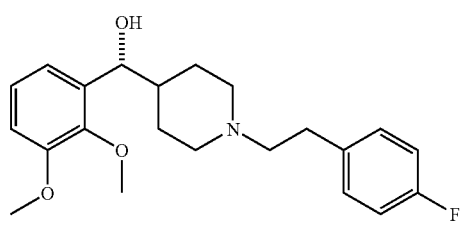

(II)

In some embodiments, the administering step in the above methods comprises administering the first compound and the second compound simultaneously. These embodiments include those in which the first compound and the second compound are in the same administrable composition, i.e., a single tablet, pill, or capsule, or a single solution for intravenous injection, or a single drinkable solution, or a single dragee formulation or patch, contains both compounds. The embodiments also include those in which each compound is in a separate administrable composition, but the patient is directed to take the separate compositions nearly simultaneously, i.e., one pill is taken right after the other or that one injection of one compound is made right after the injection of another compound, etc.

In other embodiments the administering step comprises administering one of the first compound and the second compound first and then administering the other one of the first compound and the second compound. In these embodiments, the patient may be administered a composition comprising one of the compounds and then at some time, a few minutes or a few hours, later be administered another composition comprising the other one of the compounds. Also included in these embodiments are those in which the patient is administered a composition comprising one of the compounds on a routine or continuous basis while receiving a composition comprising the other compound occasionally.

In another aspect, the present invention relates to a pharmaceutical composition comprising a first compound and a second compound.

In some embodiments, the first compound in the above pharmaceutical composition is an inverse agonist selective for a serotonin receptor. In certain embodiments, the serotonin receptor is a 5HT2A receptor, while in other embodiments the serotonin receptor is a 5HT2C receptor. In other embodiments, the inverse agonists binds to a 5HT2A receptor and a 5HT2C receptor.

In some embodiments, the first compound is a compound of formula (I)

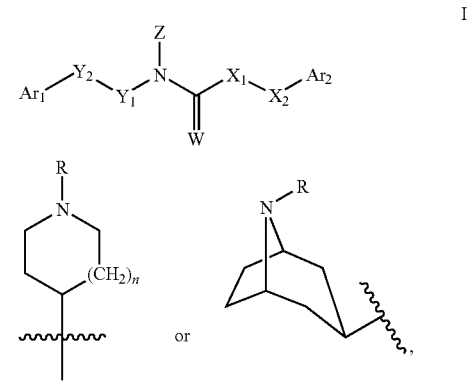

wherein R is a hydrogen, a cyclic or straight-chained or branched acyclic organyl group, a lower hydroxyalkyl group, a lower aminoalkyl group, or an aralkyl or heteroaralkyl group; and n is 1;

$X_1$ is methylene, vinylene, or an NH or N(lower alkyl) group; and $X_2$ is methylene; or, when $X_1$ is methylene or vinylene, $X_2$ is methylene or a bond; or when $X_1$ is methylene, $X_2$ is O, S, NH, or N(lower alkyl) or a bond;

$Y_1$ is methylene and $Y_2$ is methylene, vinylene, ethylene, propylene, or a bond; or $Y_1$ is a bond and $Y_2$ is vinylene; or $Y_1$ is ethylene and $Y_2$ is O, S, NH, or N(lower alkyl);

$Ar_1$ and $Ar_2$ independently are unsubstituted or substituted aryl or heteroaryl groups, provided that $Ar_1$ and $Ar_2$ are not simultaneously unsubstituted phenyl; and W is oxygen; or a pharmaceutically acceptable salt or prodrug thereof.

In other embodiments, the first compound is a compound disclosed in U.S. patent application Publication Ser. No. 2002/0004513 A1, published on Jan. 10, 2002, by Andersson et al., and entitled "AZACYCLIC COMPOUNDS," which is the publication of the U.S. application Ser. No. 09/800,096, or in U.S. patent application Publication Ser. No. 2003/0220316 A1, published on Nov. 27, 2003, by Andersson et al., and entitled "AZACYCLIC COMPOUNDS," which is the publication of the U.S. application Ser. No. 10/409,782, or in U.S. application Ser. No. 10/802,970, filed on Mar. 16, 2004, by Andersson et al., and entitled "AZACYCLIC COMPOUNDS," the entire disclosure of all of which is hereby incorporated by reference herein in their entirety, including any drawings.

In another embodiment, the first compound is N-(1-methylpiperidin-4-yl)-N-(4-fluorophenylmethyl)-N'-(4-(2-methylpropyloxy)phenylmethyl)carbamide, which is the compound of Formula (I):

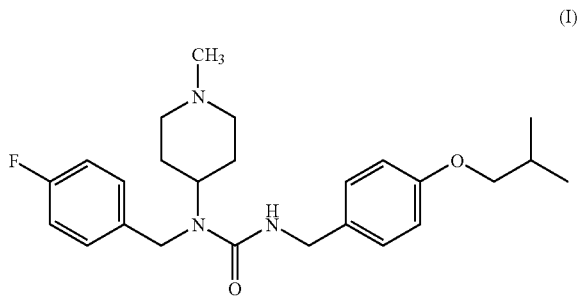

(I)

In another embodiment, the first compound in the above pharmaceutical composition is an antagonist selective for a serotonin receptor. In certain embodiments, the serotonin receptor is a 5HT2A receptor, while in other embodiments the serotonin receptor is a 5HT2C receptor. In other embodiments, the antagonists binds to a 5HT2A receptor and a 5HT2C receptor.

In some embodiments, the second compound in the above pharmaceutical composition is a selective serotonin reuptake inhibitor (SSRI). Examples of SSRIs include, but are not limited to, bupropion (Wellbutrin, Zyban), citalopram (Celexa), duloxetine, escitalopram (Lexapro), fluoxetine (Prozac), fluvoxamine (Luvox), nefazodone (Serzone), paroxetine (Paxil), sertaline (Zoloft), sibutramine, trazodone (Dividose), and venlafaxine. Any other SSRI currently known or later developed are within the scope of the present disclosure.

In other embodiments, the second compound in the above pharmaceutical composition is a serotonin/norepinephrine reuptake inhibitor (SNRI). Examples of SNRIs include, but are not limited to, citalopram (Celexa), dulexetine, escitalopram (Lexapro), fluvoxamine (Luvox), and venfalaxine (effexor). Any other SNRI currently known or later developed are within the scope of the present disclosure.

In further embodiments, the second compound in the above pharmaceutical composition is a monoamine oxidase inhibitor (MAO-I). Examples of MAO-Is include, but are not limited to, tranylcypromine (Parnate), phenelzine (Nardil), maprotiline, and isocarboxazid (Marplan). Any other MAO-I currently known or later developed are within the scope of the present disclosure.

In yet other embodiments, the second compound in the above pharmaceutical composition is a tricyclic antidepressant (TCA). Examples of TCAs include, but are not limited to, amitryptiline (Norpramine), amoxapineclomipramine (Anafranil), desipramine, doxepin (Sinequan), imipramine (Tofranil), maprotiline, (Elavil), protryptiline, and trimipramine. Any other TCA currently known or later developed are within the scope of the present disclosure.

In some other embodiments, the second compound in the above pharmaceutical composition is a compound selected from aripiprazole (Abilify), clozapine, fluoxetine/olanzapine (Symbyax), olanzapine (Zyprexa), quetiapine (Seroquel), risperidone (Risperdal), valproic acid (Depakote), and ziprasidone (Geodon). Any other atypical antidepressant currently known or later developed are within the scope of the present disclosure.

In some embodiments, the second compound in the above pharmaceutical composition is a compound selected from chlorpromazine (Thorazine®), mesoridazine (Serentil®), prochlorperazine (Compazine®), thioridazine (Mellaril®), haloperidol (Haldol®), pimozide (Orap®), clozapine (Clozaril®), loxapine (Loxitane®), olanzapine (Zyprexa®), quetiapine (Seroquel(®), resperidone (Resperidal®), ziprasidone (Geodon®), lithium carbonate, Aripiprazole (Abilify), Clozapine, Clozaril, Compazine, Etrafon, Geodon, Haldol, Inapsine, Loxitane, Mellaril, Moban, Navane, Olanzapine (Zyprexa), Orap, Permitil, Prolixin, Phenergan, Quetiapine (Seroquel), Reglan, Risperdal, Serentil, Seroquel, Stelazine, Taractan, Thorazine, Triavil, Trilafon, and Zyprexa.

In some embodiments, the second compound in the above pharmaceutical composition is an antipsychotic agent. The antipsychotic agent may be selected from the group consisting of a phenothiazine, phenylbutylpiperadine, debenzapine, benzisoxidil, and salt of lithium. The phenothiazine group of compounds may be selected from the group consisting of chlorpromazine (Thorazine®), mesoridazine (Serentil®), prochlorperazine (Compazine®), and thioridazine (Mellaril®). The phenylbutylpiperadine group of compounds may be selected from the group consisting of haloperidol (Haldol®), and pimozide (Orap®). The debenzapine group of compounds may be selected from the group consisting of clozapine (Clozaril®), loxapine (Loxitane®), olanzapine (Zyprexa®) and quetiapine (Seroquel®). The benzisoxidil group of compounds may be selected from the group consisting of resperidone (Resperidal®) and ziprasidone (Geodon (®). The salt of lithium may be lithium carbonate. In some embodiments, the antipsychotic agent may be selected from the group consisting of Aripiprazole (Abilify), Clozapine, Clozaril, Compazine, Etrafon, Geodon, Haldol, Inapsine, Loxitane, Mellaril, Moban, Navane, Olanzapine (Zyprexa), Orap, Permitil, Prolixin, Phenergan, Quetiapine (Seroquel), Reglan, Risperdal, Serentil, Seroquel, Stelazine, Taractan, Thorazine, Triavil, Trilafon, and Zyprexa, or pharmaceutically acceptable salts thereof.

In other embodiments, the second compound in the above pharmaceutical composition is a norepinephrine reuptake inhibitor. The norepinephrine reuptake inhibitor is selected from the group consisting of thionisoxetine and reboxetine.

In further embodiments, the second compound in the above pharmaceutical composition is a dopamine agonist. The dopamine agonist may be selected from the group consisting of sumatriptan, almotriptan, naratriptan, frovatriptan, rizatriptan, zomitriptan, cabergoline, amantadine, lisuride, pergolide, ropinirole, pramipexole, and bromocriptine.

In yet another embodiment, the second compound in the above pharmaceutical composition is an anti-insomnia drug. Examples of anti-insomnia drugs include, but are not limited to, alprazolam (Xanax), chlordiazepoxide (Librium, Limbitrol), clorazepate (Tranxene), estazolam (ProSom), flurazepam (Dalmane), hydroxyzine (Atarax), lorazepam (Ativan), pentobarbital (Nembutal), quazepam (Doral), secobarbital (Seconal), temazepam (Restoril), triazolam (Halcion), valium, zaleplon (Sonata), zolpidem (Ambien), and the benzodiazepine family of drugs. Any other anti-insomnia drug currently known or later developed are within the scope of the present disclosure.

In other embodiments, the second compound in the above pharmaceutical composition is an anti-manic drug. Examples of anti-manic drugs include, but are not limited to, divalproex (Depakote), lithium carbonate (Eskalith), and lithium citrate. Any other anti-manic drug currently known or later developed are within the scope of the present disclosure.

In some embodiments, the second compound in the above pharmaceutical composition is an anti-phobia drug. An example of anti-phobia drugs includes, but is not limited to, D-cycloserine. Those of skill in the art recognize that some of the other drugs disclosed herein also work as anti-phobia drugs. Any other anti-manic drug currently known or later developed are within the scope of the present disclosure.

In another embodiment, the second compound in the above pharmaceutical composition is a serotonin 2A antagonist. Tthe serotonin 2A antagonist may be M 100,907 or an analog thereof. By "M 100,907," it is meant the compound of Formula II.

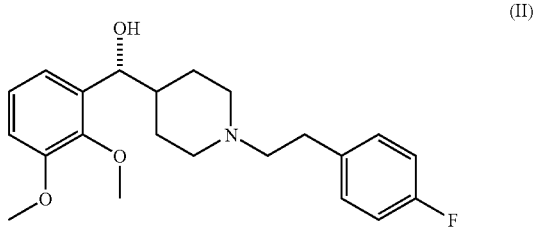

(II)

In some embodiments, the pharmaceutical compositions described herein are used to treat disorders disclosed in U.S. patent application Ser. No. 10/759,561, filed on Jan. 15, 2004, by Weiner et al., and entitled "SELECTIVE SEROTONIN 2A/2C RECEPTOR INVERSE AGONISTS AS THERAPEUTICS FOR NEURODEGENERATIVE DISEASES," which is hereby incorporated by reference herein in its entirety, including any drawings.

It is understood by those of skill in the art that the compounds disclosed herein may be present as the compounds themselves, or as pharmaceutically acceptable salts, esters, amides, or prodrugs thereof, all of which are contemplated by the present invention.

The term "pharmaceutically acceptable salt" refers to a formulation of a compound that does not cause significant irritation to an organism to which it is administered and does not abrogate the biological activity and properties of the compound. Pharmaceutical salts can be obtained by reacting a compound of the invention with inorganic acids such as hydrochloric acid, hydrobromic acid, sulfuric acid, nitric acid, phosphoric acid, methanesulfonic acid, ethanesulfonic acid, p-toluenesulfonic acid, salicylic acid and the like. Pharmaceutical salts can also be obtained by reacting a compound of the invention with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, and salts with amino acids such as arginine, lysine, and the like.

The term "ester" refers to a chemical moiety with formula —(R)$_n$—COOR', where R and R' are independently selected from the group consisting of alkyl, cycloalkyl, aryl, heteroaryl (bonded through a ring carbon) and heteroalicyclic (bonded through a ring carbon), and where n is 0 or 1.

An "amide" is a chemical moiety with formula —(R)$_n$—C(O)NHR' or —(R)$_n$—NHC(O)R', where R and R' are independently selected from the group consisting of alkyl, cycloalkyl, aryl, heteroaryl (bonded through a ring carbon) and heteroalicyclic (bonded through a ring carbon), and where n is 0 or 1. An amide may be an amino acid or a peptide molecule attached to a molecule of the present invention, thereby forming a prodrug.

Any amine, hydroxy, or carboxyl side chain on any of the compounds disclosed herein can be esterified or amidified. The procedures and specific groups to be used to achieve this end are known to those of skill in the art and can readily be found in reference sources such as Greene and Wuts, Protective Groups in Organic Synthesis, 3$^{rd}$ Ed., John Wiley & Sons, New York, N.Y., 1999, which is incorporated herein in its entirety.

A "prodrug" refers to an agent that is converted into the parent drug in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. An example, without limitation, of a prodrug would be a compound of the present invention which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. A further example of a prodrug might be a short peptide (polyaminoacid) bonded to an acid group where the peptide is metabolized to reveal the active moiety.

In some embodiments, the pharmaceutical composition described herein further comprises a physiologically acceptable carrier, diluent, or excipient, or a combination thereof.

The term "pharmaceutical composition" refers to a mixture of a compound of the invention with other chemical components, such as diluents or carriers. The pharmaceutical composition facilitates administration of the compound to an organism. Multiple techniques of administering a compound exist in the art including, but not limited to, oral, injection, aerosol, parenteral, and topical administration. Pharmaceutical compositions can also be obtained by reacting compounds with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid and the like.

The term "carrier" defines a chemical compound that facilitates the incorporation of a compound into cells or tissues. For example dimethyl sulfoxide (DMSO) is a commonly utilized carrier as it facilitates the uptake of many organic compounds into the cells or tissues of an organism.

The term "diluent" defines chemical compounds diluted in water that will dissolve the compound of interest as well as stabilize the biologically active form of the compound. Salts dissolved in buffered solutions are utilized as diluents in the art. One commonly used buffered solution is phosphate buffered saline because it mimics the salt conditions of human blood. Since buffer salts can control the pH of a solution at low concentrations, a buffered diluent rarely modifies the biological activity of a compound.

The term "physiologically acceptable" defines a carrier or diluent that does not abrogate the biological activity and properties of the compound.

The pharmaceutical compositions described herein can be administered to a human patient per se, or in pharmaceutical compositions where they are mixed with other active ingredients, as in combination therapy, or suitable carriers or excipient(s). Techniques for formulation and administration of the compounds of the instant application may be found in "Remington's Pharmaceutical Sciences," Mack Publishing Co., Easton, Pa., 18th edition, 1990.

Suitable routes of administration may, for example, include oral, rectal, transmucosal, or intestinal administration; parenteral delivery, including intramuscular, subcutaneous, intravenous, intramedullary injections, as well as intrathecal, direct intraventricular, intraperitoneal, intranasal, or intraocular injections.

Alternately, one may administer the compound in a local rather than systemic manner, for example, via injection of the compound directly in the renal or cardiac area, often in a depot or sustained release formulation. Furthermore, one may administer the drug in a targeted drug delivery system, for example, in a liposome coated with a tissue-specific antibody. The liposomes will be targeted to and taken up selectively by the organ.

The pharmaceutical compositions of the present invention may be manufactured in a manner that is itself known, e.g., by means of conventional mixing, dissolving, granulating, dragee-making, levigating, emulsifying, encapsulating, entrapping or tabletting processes.

Pharmaceutical compositions for use in accordance with the present invention thus may be formulated in conventional manner using one or more physiologically acceptable carriers comprising excipients and auxiliaries which facilitate processing of the active compounds into preparations which can be used pharmaceutically. Proper formulation is dependent upon the route of administration chosen. Any of the well-known techniques, carriers, and excipients may be used as suitable and as understood in the art; e.g., in Remington's Pharmaceutical Sciences, above.

For injection, the agents of the invention may be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained by mixing one or more solid excipient with pharmaceutical combination of the invention, optionally grinding the resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added: All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation.

Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

A pharmaceutical carrier for the hydrophobic compounds of the invention is a cosolvent system comprising benzyl alcohol, a nonpolar surfactant, a water-miscible organic polymer, and an aqueous phase. A common cosolvent system used is the VPD co-solvent system, which is a solution of 3% w/v benzyl alcohol, 8% w/v of the nonpolar surfactant Polysorbate 80™, and 65% w/v polyethylene glycol 300, made up to volume in absolute ethanol. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of POLYSORBATE 80™; the fraction size of polyethylene glycol may be varied; other biocompatible polymers may replace polyethylene glycol, e.g., polyvinyl pyrrolidone; and other sugars or polysaccharides may substitute for dextrose.

Alternatively, other delivery systems for hydrophobic pharmaceutical compounds may be employed. Liposomes and emulsions are well known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

Many of the compounds used in the pharmaceutical combinations of the invention may be provided as salts with pharmaceutically compatible counterions. Pharmaceutically compatible salts may be formed with many acids, including but not limited to hydrochloric, sulfuric, acetic, lactic, tartaric, malic, succinic, etc. Salts tend to be more soluble in aqueous or other protonic solvents than are the corresponding free acid or base forms.

Pharmaceutical compositions suitable for use in the present invention include compositions where the active ingredients are contained in an amount effective to achieve its intended purpose. More specifically, a therapeutically effective amount means an amount of compound effective to prevent, alleviate or ameliorate symptoms of disease or prolong the survival of the subject being treated. Determination of a therapeutically effective amount is well within the capability of those skilled in the art, especially in light of the detailed disclosure provided herein.

The exact formulation, route of administration and dosage for the pharmaceutical compositions of the present invention can be chosen by the individual physician in view of the patient's condition. (See e.g., Fingl et al. 1975, in "The Pharmacological Basis of Therapeutics", Ch. 1 p. 1). Typically, the dose range of the composition administered to the patient can be from about 0.5 to 1000 mg/kg of the patient's body weight. The dosage may be a single one or a series of two or more given in the course of one or more days, as is needed by the patient. Note that for almost all of the specific compounds mentioned in the present disclosure, human dosages for treatment of at least some condition have been established. Thus, in most instances, the present invention will use those same dosages, or dosages that are between about 0.1% and 500%, more preferably between about 25% and 250% of the established human dosage. Where no human dosage is established, as will be the case for newly-discovered pharmaceutical compounds, a suitable human dosage can be inferred from $ED_{50}$ or $ID_{50}$ values, or other appropriate values derived from in vitro or in vivo studies, as qualified by toxicity studies and efficacy studies in animals.

Although the exact dosage will be determined on a drug-by-drug basis, in most cases, some generalizations regarding the dosage can be made. The daily dosage regimen for an adult human patient may be, for example, an oral dose of between 0.1 mg and 500 mg of each ingredient, preferably between 1 mg and 250 mg, e.g. 5 to 200 mg or an intravenous, subcutaneous, or intramuscular dose of each ingredient between 0.01 mg and 100 mg, preferably between 0.1 mg and 60 mg, e.g. 1 to 40 mg of each ingredient of the pharmaceutical compositions of the present invention or a pharmaceutically acceptable salt thereof calculated as the free base, the composition being administered 1 to 4 times per day. Alternatively the compositions of the invention may be administered by continuous intravenous infusion, preferably at a dose of each ingredient up to 400 mg per day. Thus, the total daily dosage by oral administration of each ingredient will typically be in the range 1 to 2000 mg and the total daily dosage by parenteral administration will typically be in the range 0.1 to 400 mg. Suitably the compounds will be administered for a period of continuous therapy, for example for a week or more, or for months or years.

Dosage amount and interval may be adjusted individually to provide plasma levels of the active moiety which are sufficient to maintain the modulating effects, or minimal effective concentration (MEC). The MEC will vary for each compound but can be estimated from in vitro data. Dosages necessary to achieve the MEC will depend on individual characteristics and route of administration. However, HPLC assays or bioassays can be used to determine plasma concentrations.

Dosage intervals can also be determined using MEC value. Compositions should be administered using a regimen which maintains plasma levels above the MEC for 10-90% of the time, preferably between 30-90% and most preferably between 50-90%.

In cases of local administration or selective uptake, the effective local concentration of the drug may not be related to plasma concentration.

The amount of composition administered will, of course, be dependent on the subject being treated, on the subject's weight, the severity of the affliction, the manner of administration and the judgment of the prescribing physician.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions comprising a compound of the invention formulated in a compatible pharmaceutical carrier may also be prepared, placed in an appropriate container, and labeled for treatment of an indicated condition.

What is claimed is:

1. A pharmaceutical composition comprising a compound of Formula (I)

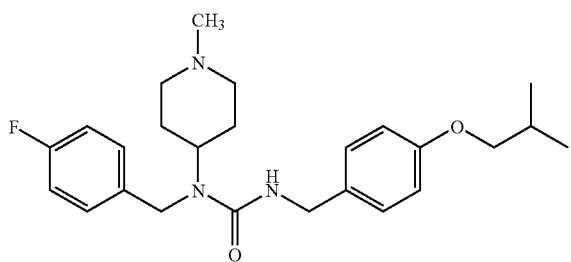

or a pharmaceutically acceptable salt thereof, and fluoxetine.

2. The pharmaceutical composition of claim 1, further comprising a physiologically acceptable carrier, diluent, or excipient, or a combination thereof.

3. A pharmaceutical composition comprising a compound of Formula (I)

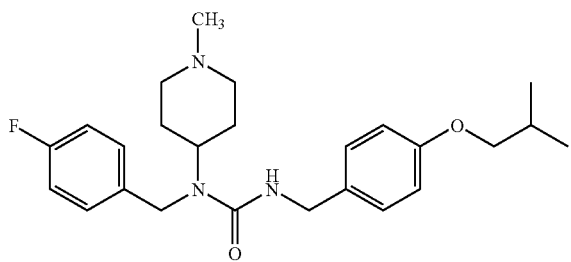

or a pharmaceutically acceptable salt thereof, and a selective serotonin reuptake inhibitor.

4. The composition of claim 3, wherein the selective serotonin reuptake inhibitor is selected from the group consisting of bupropion, citalopram, duloxetine, escitalopram, fluvoxamine, nefazodone, paroxetine, sertaline, sibutramine, trazodone, and venlafaxine.

5. The pharmaceutical composition of claim 3, further comprising a physiologically acceptable carrier, diluent, or excipient, or a combination thereof.

6. The composition of claim 1, wherein the compound of formula (I) is the free base.

7. The composition of claim 1, wherein the composition is in a single unit dosage form.

8. The composition of claim 7, wherein the composition is in a single unit dosage form suitable for oral administration to a human.

9. The composition of claim 8, wherein the dosage form is solid.

10. The composition of claim 9, wherein the composition is in the form of a tablet or a capsule.

11. The composition of claim 10, wherein the composition is in the form of a tablet.

12. The composition of claim 1, wherein the amount of the compound of formula (I), or a pharmaceutically acceptable salt thereof, is from about 0.1 mg to about 500 mg.

13. The composition of claim 1, wherein the amount of the compound of formula (I), or a pharmaceutically acceptable salt thereof, is from about 1 mg to about 40 mg.

* * * * *